United States Patent [19]

Habicht et al.

[11] 4,141,982

[45] Feb. 27, 1979

[54] BENZ-ACYLBENZIMIDAZOLE-2-CARBOXYLIC ACID DERIVATIVES

[75] Inventors: Ernst Habicht, Oberwil; Pier G. Ferrini, Binningen; Alfred Sallmann, Bottmingen, all of Switzerland

[73] Assignee: Ciba-Geigy Corporation, Ardsley, N.Y.

[21] Appl. No.: 825,630

[22] Filed: Aug. 18, 1977

[30] Foreign Application Priority Data

Aug. 27, 1976 [LU] Luxembourg .................. 75684

[51] Int. Cl.$^2$ .................. A61K 31/415; C07D 235/16
[52] U.S. Cl. .................. 424/267; 546/271; 546/328; 546/315; 424/263; 424/273 R; 544/342; 548/327; 548/330; 548/331
[58] Field of Search .................. 548/331, 327; 424/273 R, 267; 260/293.6

[56] References Cited

FOREIGN PATENT DOCUMENTS 766749  1/1957  United Kingdom.

OTHER PUBLICATIONS

Chemical Abstracts Sixth Collective Index, vols. 51–55, 1957–1961, Subjects A–Bi, p. 1533s.
Chemical Abstracts Fifth Decennial Index, vols. 41–50, 1947–1956, Subjects B–Bz, p. 1636s.

Grantham et al., J. Chem. Soc. C (London), 1969, pp. 70–74.

*Primary Examiner*—Natalie Trousof
*Attorney, Agent, or Firm*—John J. Maitner

[57] ABSTRACT

New heterocyclylcarboxylic acid derivatives which are acylated in the nucleus, especially benz-acyl-benzimidazole-2-carboxylic acid derivatives of the formula

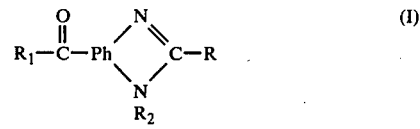

in which R is a free, esterified or amidated carboxyl group or a free, etherified or esterified hydroxymethyl group, $R_1$ is an aliphatic, cycloaliphatic, aromatic, araliphatic, heterocyclic or heterocyclic-aliphatic radical, $R_2$ is hydrogen or an aliphatic radical and Ph is a 1,2-phenylene group containing the radical $R_1$—C(=O)—, with the proviso that $R_1$ contains at least 2 carbon atoms if Ph is otherwise unsubstituted, $R_2$ is ethyl and R is acetoxymethyl, and salts of such compounds having salt-forming properties, are useful as anti-allergic agents.

9 Claims, No Drawings

BENZ-ACYLBENZIMIDAZOLE-2-CARBOXYLIC ACID DERIVATIVES

The invention relates to processes for the preparation of heterocyclylcarboxylic acid derivatives which are acylated in the nucleus, especially benz-acyl-benzimidazole-2-carboxylic acid derivatives of the formula

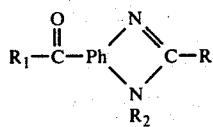

in which R is a free, esterified or amidated carboxyl group or a free, etherified or esterified hydroxymethyl group, $R_1$ is an aliphatic, cycloaliphatic, aromatic, araliphatic, heterocyclic or heterocyclic-aliphatic radical, $R_2$ is hydrogen or an aliphatic radical and Ph is a 1,2-phenylene group containing the radical $R_1$—C(=O)—, with the proviso that $R_1$ contains at least 2 carbon atoms if Ph is otherwise unsubstituted, $R_2$ is ethyl and R is acetoxymethyl, and salts of such compounds having salt-forming properties, and also the compounds of the formula I and salts of such compounds having salt-forming properties, and also pharmaceutical formulations containing such compounds and the use of the latter as pharmaceuticals.

In the context of the present description, organic radicals and compounds designated as "lower" contain, especially, up to and including 7 and preferably up to and including 4 carbon atoms.

In esterified carboxyl and etherified hydroxymethyl R, the etherified hydroxyl group is, for example, a hydroxyl group etherified by an aliphatic or araliphatic radical, such as a substituted or unsubstituted aliphatic or araliphatic hydrocarbon radical, for example corresponding lower alkoxy or phenyl-lower alkoxy. Substituents of lower alkoxy are, inter alia, hydroxyl, lower alkoxy and/or di-lower alkyl-amino, and those of phenyl-lower alkoxy are, for example, lower alkyl, lower alkoxy and/or halogen, it being possible for one or more substituents to be present.

In amidated carboxyl, the amino group is, for example, amino which is unsubstituted or monosubstituted by hydroxyl or monosubstituted or disubstituted by aliphatic radicals, especially by substituted or unsubstituted aliphatic hydrocarbon radicals, it being possible for such radicals to be monovalent or divalent, such as amino which is unsubstituted or monosubstituted by hydroxyl or monosubstituted or disubstituted by corresponding lower alkyl or lower alkylene.

In esterified hydroxymethyl R, the esterified hydroxyl group is, for example, hydroxyl esterified by a carboxylic acid, such as an aliphatic or aromatic carboxylic acid, for example corresponding lower alkanoyloxy or benzoyloxy which is unsubstituted or substituted by lower alkyl, lower alkoxy and/or halogen. Lower alkanoyloxy is, for example, acetoxy, propionyloxy, butyryloxy, isobutyryloxy, valeroyloxy, caproyloxy or pivaloyloxy.

Aliphatic, cycloaliphatic, aromatic and araliphatic radicals $R_1$ and $R_2$ are, in particular, substituted or unsubstituted aliphatic, cycloaliphatic, aromatic or araliphatic hydrocarbon radicals, such as corresponding lower alkyl, lower alkenyl, cycloalkyl, phenyl, naphthyl or phenyl-lower alkyl. Substituents are, for example, hydroxyl, lower alkoxy, lower alkylthio or phenylthio, lower alkylsulphinyl or phenylsulphinyl or lower alkylsulphonyl or phenylsulphonyl, especially for lower alkyl $R_1$ and lower alkyl $R_2$, and also lower alkyl, lower alkoxy and/or halogen, especially for phenyl or phenyl-lower alkyl $R_1$. Heterocyclyl in a heterocyclic or heterocyclic-aliphatic radical $R_1$ is, in particular, monocyclic heterocyclyl of aromatic character containing a hetero-atom, such as oxygen, sulphur or nitrogen, as a ring member, such as furyl, thienyl or pyridyl. In a heterocyclic-aliphatic radical $R_1$, the aliphatic part is, for example, a corresponding aliphatic hydrocarbon radical, especially lower alkyl.

Apart from being substituted by the radical of the formula $R_1$-C(=O), 1,2-phenylene can additionally be monosubstituted or polysubstituted, inter alia by lower alkyl, lower alkoxy, hydroxyl and/or halogen.

Lower alkoxy is, for example, methoxy, ethoxy, n-propoxy, isopropoxy, n-butoxy, isobutoxy, tert.-butoxy, n-pentyloxy or n-hexyloxy.

Phenyl-lower alkoxy is, for example, benzyloxy or 1-or 2-phenylethoxy.

Hydroxy-lower alkoxy, lower alkoxy-lower alkoxy and di-lower alkylamino-lower alkoxy are, especially, 2- and/or 3-hydroxy-lower alkoxy, for example 2-hydroxyethoxy, 3-hydroxypropoxy or 2,3-dihydroxypropoxy, and 2- or 3-lower alkoxy-lower alkoxy, for example 2-methoxyethoxy, 2-ethoxyethoxy or 3-methoxypropoxy, and, respectively, di-lower alkylamino-lower alkoxy, for example dimethylaminoethoxy or diethylaminoethoxy.

Lower alkyl is, for example, methyl, ethyl, n-propyl, isopropyl, n-butyl, isobutyl, tert.-butyl, n-pentyl, n-hexyl or n-heptyl.

Halogen is, especially, halogen with an atomic number of up to and including 35, i.e. fluorine, chlorine or bromine.

Lower alkylene is, for example, 1,4-butylene, 1,5-pentylene or 1,6-hexylene.

Lower alkenyl is, for example, vinyl, 1-methyl-vinyl, 1-ethyl-vinyl, allyl, 2- or 3-methyl-allyl or 3,3-dimethylallyl.

Cycloalkyl preferably contains 3 to 8 ring atoms and is, for example, cyclopropyl, cyclopentyl, cyclohexyl, cycloheptyl or cyclooctyl.

Lower alkylthio is, for example, methylthio or ethylthio; whilst lower alkylsulphinyl and lower alkylsulphonyl are, for example, methylsulphinyl, ethylsulphinyl, methylsulphonyl or ethylsulphonyl.

Lower alkyl substituted by lower alkylthio, lower alkylsulphinyl or lower alkylsulphonyl is, for example, methylthiomethyl or ethylthiomethyl, 1- or 2-methylthioethyl or 1- or 2-ethylthioethyl or 2- or 3-methylthiopropyl or 2- or 3-ethylthiopropyl, methylsulphinylmethyl or ethylsulphinylmethyl, 1- or 2-methylsulphinylethyl or 1- or 2-ethylsulphinylethyl or 2- or 3-methylsulphinylpropyl or 2- or 3-ethylsulphinylpropyl, or methylsulphonylmethyl or ethylsulphonylmethyl, 1-or 2-methylsulphonylethyl or 1- or 2-ethylsulphonylethyl or 2- or 3-methylsulphonylpropyl or 2- or 3-ethylsulphonylpropyl. Lower alkyl substituted by phenylthio, phenylsulphinyl or phenylsulphonyl is, for example phenylthiomethyl, phenylsulphinylmethyl or phenylsulphonylmethyl, or 1- or 2-phenylthioethyl, or 1- or 2-phenylsulphinylethyl or 1- or 2-phenylsulphonylethyl.

Phenyl-lower alkyl is, for example, benzyl, 1- or 2-phenylethyl or 1-, 2- or 3-phenylpropyl.

Furyl is, for example 2-furyl and thienyl is, for example 2-thienyl, whilst pyridyl can be 2-, 3- or 4-pyridyl.

Furyl-lower alkyl, thienyl-lower alkyl and pyridyl-lower alkyl are, especially, correspondingly substituted methyl radicals, such as furfuryl, 2-thienyl or picolyl, for example 2- or 4-pyridylmethyl.

Salts are those of compounds of the formula I, in which R represents carboxyl, with bases; such salts are, especially, non-toxic salts, which can be used pharmaceutically, with bases, such as alkali metal salts or alkaline earth metal salts, for example sodium, potassium, magnesium or calcium salts, and also ammonium salts with ammonia or amines, such as lower alkyl-amines or hydroxy-lower alkyl-amines, for example trimethylamine, triethylamine or di- or tri-(2-hydroxyethyl)amine.

The novel compounds show valuable pharmacological properties. In particular, they show anti-allergic actions, which can be demonstrated, for example, on rats in doses of about 0.03 to about 10 mg/kg on intravenous administration and in doses of about 1 to about 100 mg/kg on oral administration in the passive cutaneous anaphylaxis test (PCA reaction), which is carried out analogously to the method described by Goose and Blair, Immunology, Volume 16, page 749 (1969), passive cutaneous anaphylaxis being produced by the procedure described by Ovary, Progr. Allergy, Volume 5, page 459 (1958). The anti-allergic action, and especially the degranulation-inhibiting action can be determined in an in vitro test, also with the aid of the release of hystamine from peritoneal cells in rats, in the dosage range of about 0.01 to about 100 μg/ml in the case of immunologically induced release (in which case, for example, rats infested with Nippostrongylus brasiliensis are used) and of about 1.0 to about 100 μg/ml in the case of chemically induced release (in which case, for example, this is effected with a polymer of N-4-methoxy-phenylethyl-N-methyl-amine). The compounds of the present invention are accordingly useful as inhibitors of allergic reactions, for example in the treatment and prophylaxis of allergic diseases, such as asthma, including both extrinsic and intrinsic asthma, or other allergic diseases such as allergic rhinitis, for example hayfever or conjunctivitis or allergic dermatitis, for example urticaria or eczema.

The invention relates especially to compounds of the formula I in which R is free carboxyl or hydroxymethyl, esterified carboxyl or etherified hydroxymethyl containing, as the etherified hydroxyl group, lower alkoxy, hydroxy-lower alkoxy, lower alkoxy-lower alkoxy or di-lower alkyl-amino-lower alkoxy, amidated carboxyl containing, as the amino group, amino, hydroxyamino, lower alkyl-amino, di-lower alkyl-amino or lower alkyleneamino, or esterified hydroxymethyl containing, as the esterified hydroxyl group, lower alkanoyloxy or benzyloxy which is unsubstituted or substituted by lower alkyl, lower alkoxy and/or halogen, $R_1$ is lower alkyl, lower alkenyl or cycloalkyl, which are unsubstituted or substituted by lower alkoxy, lower alkylthio, lower alkylsulphinyl, lower alkylsulphonyl, phenylthio, phenylsulphinyl or phenylsulphonyl, or phenyl or phenyl-lower alkyl which are unsubstituted or substituted in the phenyl part by lower alkyl, lower alkoxy or halogen, or furyl, thienyl or pyridyl, or furyl-lower alkyl, thienyl-lower alkyl or pyridyl-lower alkyl, $R_2$ is hydrogen or lower alkyl and Ph is 1,2-phenylene which contains the radical of the formula $R_1-C(=O)-$ and is otherwise unsubstituted or substituted by lower alkyl, lower alkoxy, hydroxyl and/or halogen, with the proviso that $R_1$ contains at least 2 carbon atoms if Ph is otherwise unsubstituted, $R_2$ is ethyl and R is acetoxymethyl, and salts, especially salts which can be used pharmaceutically, of compounds of the formula I in which R represents carboxyl.

The invention relates especially to compounds of the formula I in which R is free carboxyl, esterified carboxyl containing, as the etherified hydroxyl group, lower alkoxy or hydroxy-lower alkoxy having up to and including 4 carbon atoms, for example methoxy, ethoxy, 2-hydroxyethoxy or 2,3-dihydroxypropoxy, or amidated carboxyl containing, as the amino group, amino or hydroxyamino or lower alkyl-amino or di-lower alkylamino in which lower alkyl contains up to and including 4 carbon atoms, for example methylamino, ethylamino, dimethylamino or diethylamino, or hydroxymethyl, etherified hydroxymethyl containing, as the etherified hydroxyl group, lower alkoxy having up to 4 carbon atoms, for example methoxy or ethoxy, or di-lower alkyl-amino-lower alkoxy having, in each case, up to 4 carbon atoms in the alkyl part and the alkoxy part, such as dimethylaminoethoxy, or esterified hydroxymethyl containing, as the esterified hydroxyl group, lower alkanoyloxy having up to 7 carbon atoms, for example acetoxy, propionyloxy or pivaloyloxy, or benzoyloxy which is unsubstituted or substituted by lower alkyl, for example methyl, lower alkoxy, for example methoxy, and/or halogen, for example chlorine, $R_1$ is lower alkyl having up to and including 7 carbon atoms, for example methyl, ethyl, n-propyl, isopropyl, n-butyl, isobutyl, tert.-butyl, n-pentyl, neopentyl, n-hexyl or n-heptyl, lower alkoxy-lower alkyl, lower alkylthio-lower alkyl, lower alkylsulphinyl-lower alkyl or lower alkylsulphonyl-lower alkyl, in which the individual lower alkyl radicals contain up to and including 4 carbon atoms, for example methoxymethyl, ethoxymethyl, methylthiomethyl, ethylthiomethyl, methylsulphinylmethyl, ethylsulphinylmethyl, methylsulphonylmethyl or ethylsulphonylmethyl, 1- or 2-methoxyethyl, 1- or 2-ethoxyethyl, 1- or 2-methylthioethyl, 1- or 2-ethylthioethyl, 1- or 2-methylsulphinylethyl, 1- or 2-ethylsulphinylethyl, 1- or 2-methylsulphonylethyl or 1- or 2-ethyl-sulphonylethyl, or 1-, 2- or 3-methoxypropyl, 1-, 2- or 3-ethoxypropyl, 1-, 2- or 3-methylthiopropyl, 1-, 2- or 3-ethylthiopropyl, 1-, 2- or 3-methylsulphinylpropyl, 1-, 2- or 3-ethylsulphinylpropyl, 1-, 2- or 3-methylsulphonylpropyl or 1-, 2- or 3-ethylsulphonylpropyl, phenylthio-lower alkyl, phenylsulphinyl-lower alkyl or phenylsulphonyl-lower alkyl, in which the lower alkyl radical contains up to and including 4 carbon atoms, for example phenylthiomethyl, phenylsulphinylmethyl or phenylsulphonylmethyl, 1- or 2-phenylthioethyl, 1- or 2-phenylsulphinylethyl or 1- or 2-phenylsulphonylethyl or 1-, 2- or 3-phenylthiopropyl, 1-, 2- or 3-phenylsulphinylpropyl or 1-, 2- or 3-phenylsulphonylpropyl, lower alkenyl having up to and including 5 carbon atoms, for example 1-methyl- or 1-ethylvinyl, or allyl, cycloalkyl having up to and including 7 carbon atoms, for example cyclopropyl or cyclohexyl, phenyl or phenyl-lower alkyl having up to and including 4 carbon atoms in the lower alkyl radical and being unsubstituted or substituted by lower alkyl having up to and including 4 carbon atoms, for example methyl, lower alkoxy having up to and including 4 carbon atoms, for example methoxy, and/or halogen having an atomic number of up to and including 35, for example chlorine or bromine, for example benzyl or 1- or 2-phenylethyl, or furyl, thienyl or pyridyl, for example 2-furyl, 2-thienyl or 2-, 3- or 4-pyridyl, or furyl-lower alkyl, thienyl-lower alkyl or pyridyl-lower alkyl having up to and including 4 carbon atoms in the lower alkyl radical, for example furfuryl, 2-thienyl or 2- or 4-picolyl, $R_2$ is hydrogen or lower alkyl having up to and including 4 carbon atoms, for example methyl, and Ph is 1,2-phenylene which contains the radical of the formula $R_1$—C(=O)— and is otherwise unsubstituted or substituted by lower alkyl having up to and including 4 carbon atoms, for example methyl, lower alkoxy having up to and including 4 carbon atoms, for example methoxy, hydroxyl and/or halogen having an atomic number of up to and including 35, for example chlorine or bromine, the radical of the formula $R_1$—C(=O)— occupying any position suitable for substitution in the 1,2-phenylene radical, preferably the 4-position or 5-position, with the proviso that $R_1$ contains at least 2 carbon atoms if Ph is otherwise unsubstituted, $R_2$ is ethyl and R is acetoxymethyl, and salts, especially salts which can be used pharmaceutically, of such compounds of the formula I in which R is carboxyl, with bases.

The invention relates, in particular, to compounds of the formula

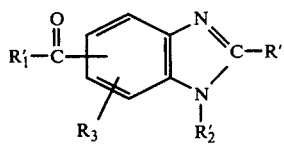

(Ia)

in which R' on the one hand is, in particular, carboxyl or also esterified carboxyl containing, as the etherified hydroxyl group, lower alkoxy having up to and including 4 carbon atoms, for example methoxy or ethoxy, or amidated carboxyl containing, as the amino group, amino or hydroxyamino, or, on the other hand, in particular, hydroxymethyl or also etherified hydroxymethyl containing, as the etherified hydroxyl group, lower alkoxy having up to 4 carbon atoms, for example methoxy or ethoxy, or di-lower alkyl-amino-lower alkoxy having up to 7 carbon atoms, for example dimethylaminoethoxy, or esterified hydroxymethyl containing, as the esterified hydroxyl group, lower alkanoyloxy having up to 7 carbon atoms, for example acetoxy, and in which $R_1'$ is, especially, lower alkyl having up to and including 7 carbon atoms, for example methyl, ethyl, n-propyl, n-butyl, tert.-butyl, n-pentyl, n-hexyl or n-heptyl, and also lower alkoxy-lower alkyl, lower alkylthio-lower alkyl, lower alkylsulphinyl-lower alkyl, phenylthio-lower alkyl or phenylsulphinyl-lower alkyl in which the lower alkyl radicals contain up to and including 4 carbon atoms, for example methoxymethyl, methylthiomethyl, methylsulphinylmethyl, phenylthiomethyl or phenylsulphinylmethyl, 2-methoxyethyl, 2-methylthioethyl, 2-methylsulphinylethyl, 2-phenylthioethyl or 2-phenylsulphinylethyl or 3-methoxypropyl, 3-methylthiopropyl, 3-methylsulphinylpropyl, 3-phenylthiopropyl or 3-phenylsulphinylpropyl, cycloalkyl having up to and including 6 ring carbon atoms, for example cyclopropyl or cyclohexyl, or phenyl, furyl or pyridyl, for example 3- or 4-pyridyl, $R_2'$ is, in particular, hydrogen and also lower alkyl having up to 4 carbon atoms, for example methyl, and $R_3$ is hydrogen, lower alkyl having up to and including 4 carbon atoms, for example methyl, lower alkoxy having up to and including 4 carbon atoms, for example methoxy, hydroxyl or halogen having an atomic number of up to and including 35, for example chlorine, the radical of the formula $R_1'$—C(=O)— and the group $R_3$, if this differs from hydrogen, being able to occupy any position suitable for substitution in the benzimidazole ring, preferably the 5-position and the 6-position, with the proviso that $R_1'$ contains at least 2 carbon atoms if $R_3$ is hydrogen, $R_2'$ is ethyl and R' is acetoxymethyl, and salts, especially salts which can be used pharmaceutically, of such compounds of the formula I in which R' represents carboxyl, with bases.

The invention relates, in particular, to the compounds of the formula Ia in which R' is carboxyl or hydroxymethyl or also esterified carboxyl or etherified hydroxymethyl containing, as the etherified hydroxyl group, lower alkoxy having up to and including 4 carbon atoms, for example methoxy or ethoxy, and in which $R_1'$ is lower alkyl having up to and including 7, and preferably having up to and including 4, carbon atoms, for example methyl, ethyl, n-propyl, isopropyl, n-butyl or tert.-butyl, cycloalkyl having up to and including 6 ring carbon atoms, for example cyclopropyl or cyclohexyl, or phenyl, $R_2'$ is, especially, hydrogen and is also lower alkyl having up to and including 4 carbon atoms, for example methyl, and $R_3$ is hydrogen, lower alkyl having up to and including 4 carbon atoms, for example methyl, lower alkoxy having up to and including 4 carbon atoms, for example methoxy, or halogen having an atomic number of up to and including 35, for example chlorine, the radicals $R_1'$—C (=O)— and $R_3$, if this differs from hydrogen, preferably occupying the 5-position and 6-position respectively of the benzimidazole ring, and salts, especially the salts which can be used pharmaceutically, of such compounds of the formula Ia in which R' represents carboxyl, with bases.

The invention relates, in particular, to compounds of the formula Ia in which R' either is carboxyl or is hydroxymethyl and in which $R_1'$ is lower alkyl having up to and including 7 carbon atoms, for example having up to and including 4 carbon atoms, for example methyl, ethyl, n-propyl, isopropyl or n-butyl, $R_2'$ is hydrogen and $R_3$ is hydrogen or lower alkyl having up to and including 4 carbon atoms, for example methyl, the radical $R_1'$—C(=O)— occupying the 5-position of the benzimidazole ring and a lower alkyl radical $R_3$ occupying the 6-position of the benzimidazole ring, and salts, especially salts which can be used pharmaceutically, of such compounds in which R' is carboxyl, with bases.

The invention relates specifically to the compounds of the formula I mentioned in the examples.

The novel compounds can be prepared in a manner which is known per se. Thus, for example, they can be obtained when a compound of the formula II

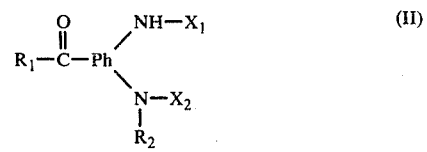

(II)

in which one of the radicals $X_1$ and $X_2$ is an optionally etherified group of the formula —C(=O)—CH$_2$OH and the other is hydrogen, or a salt thereof, is cyclised and, if desired, a compound which is thus obtainable is converted into another compound of the formula I and/or a resulting free, salt-forming compound is converted into a salt or a resulting salt is converted into the free compound or into another salt.

Salts of starting materials of the formula II which can be used are, for example, acid addition salts, such as hydrohalides, for example the hydrochlorides, of compounds in which R is free, etherified or esterified hydroxymethyl and alkali metal salts or ammonium salts, for example the sodium salts, of compounds in which R is carboxyl.

The cyclisation is effected in the customary manner at normal temperature or, especially at elevated temperature, for example at about 50° C. to about 160° C. and in particular at about 110° C. to 140° C., if necessary in the presence of an acid condensing agent, such as a hydrogen halide acid, for example hydrochloric acid, and/or of a water-binding agent, for example dicyclohexylcarbodiimide, and advantageously under an inert gas, for example under nitrogen.

The compounds resulting from the above process variant in which R is free or etherified hydroxymethyl, can subsequently be converted easily in the customary manner into other compounds of the formula I.

The starting materials of the formula II are appropriately prepared in situ, for example by reacting a corresponding 1,2-phenylenediamine, which is substituted by the acyl radical of the formula $R_1$—C(=O)— and, if desired, can contain yet further substituents, or an acid addition salt thereof, for example the hydrochloride thereof, with glycollic acid, wherein the hydroxy group is free or etherified, or with a suitable reactive derivative thereof, preferably an ester, such as a lower alkyl ester, an amide or an anhydride, such as the acid halide, thereof, especially with glycollic acid or a lower alkoxyacetic acid, if necessary in the presence of a solvent or diluent, such as a lower alkanol, for example methanol or ethanol, and/or with warming to about 50° C. to about 160° C., for example to about 110° C. to about 140° C. The 1,2-phenylenediamines to be used as starting materials for this process can be obtained, for example, by customary reduction of the corresponding 1,2-nitroaniline compound, such as by reacting the said compound with a chemical reducing agent, such as sodium dithionite, or with suitably activated hydrogen, such as hydrogen catalytically activated by means of a noble metal catalyst in a basic medium, for example by Raney nickel in methanol or ethanol. In a modification of this method, it is also possible to react this 1,2-nitroaniline intermediate with the abovementioned acid, especially with glycollic acid, or with a suitable derivative thereof, and subsequently to reduce the nitro group, for example with hydrogen in the presence of Raney nickel.

However, reduction of the nitro group can also be effected by intramolecular disproportionation, by subjecting a corresponding disubstituted 1,2-nitroaniline of the formula $R_1$—C(=O)—Ph(NO$_2$)—NR$_2$—ethyl to acid treatment, for example to the action of a Lewis acid, such as of zinc chloride in a carboxylic acid anhydride, for example acetic anhydride, cyclisation taking place to give the corresponding compound of the formula I in which R is hydroxymethyl esterified by a carboxylic acid and $R_2$ differs from hydrogen.

When they are not known compounds, the 1,2-nitroaniline compounds to be used for the preparation of the starting materials of the formula II can be prepared, for example, starting from the corresponding chlorobenzenes of the formula H—PhH—Cl by acylating these in the customary manner, for example by a reaction with a compound of the formula $R_1$—COHal or $(R_1CO)_2O$ in the presence of aluminium trichloride, nitrating the compound of the formula $R_1$—CO—Ph—H—Cl, which is thus obtainable, with nitric acid/sulphuric acid and reacting the chloronitro compound of the formula $R_1$—CO—Ph(Cl)—NO$_2$ which is thus obtainable, with ammonia or an amine of the formula $R_2NH_2$.

The novel compounds can also be prepared by oxydising $X_3$ in a compound of the formula

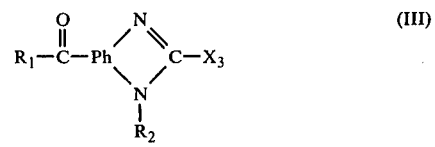

in which $X_3$ is a formyl group or an optionally etherified hydroxymethyl radical, R to an optionally esterified carboxy group R and, if desired, converting a compound of the formula I, which is thus obtainable, into another compound of the formula I and/or, if desired, converting a resulting salt into the free compound or into another salt and/or converting a free, salt-forming compound into a salt.

A group $X_3$ is, in particular the formyl group. This group can also be formed, for example from the methyl, aminomethyl or especially hydroxymethyl group or from a hydroxymethyl group esterified with an inorganic acid, such as a hydrogen halide acid, for example with hydrochloric acid, or a hydroxymethyl group etherified with a cyclic 2-hydroxy-ether, for example with 2-hydroxytetrahydropyrane, or a cyclic 2- or 4-hydroxy-thioether, for example with 2-hydroxytetrahydrothiopyrane, 2-hydroxytetrahydrothiophene or 4-hydroxy-4-methoxytetrahydrothiophene, or set free from one of its derivatives, such as a lower alkylene- or di-lower alkyl-acetal or an imine, for example benzylimine, in situ in the course of the oxidation reaction.

The oxidation can be carried out in a manner which is known per se, for example by treatment with an oxidising heavy metal compound, preferably with an oxidising compound containing chromium-VI or manganese-VII, for example chromium trioxide or especially potassium permanganate, in the case of starting materials of the formula II in which $X_3$ is the formyl group or a radical which can be converted into the latter by oxidation mentioned, such as hydroxymethyl, and also with an oxidising compound containing manganese IV, such as manganese dioxide, in the case of starting materials of the formula II in which $X_3$ is a etherified hydroxymethyl group. The reaction is advantageously carried out in the presence of a suitable solvent or diluent, for example of acetone or pyridine or of a mixture, preferably an aqueous mixture, thereof, if necessary with cooling or warming, for example in a temperature range of about 0° C. to about 80° C.

The starting materials of the formula III can be prepared in a manner which is known per se.

Compounds of the formula III in which $X_3$ is a formyl, can be prepared, for example, by reacting a corresponding compound of the formula

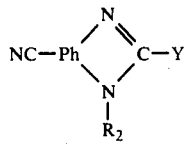

in which Y is a acetalised formyl group, such as lower alkylene-dioxymethyl or di-lower alkoxy-methyl, with a compound of the formula

 (IIIb), wherein $Y_1$ is a group —M—Hal or —M/2, M is a metal atom of group II of the periodic table of the elements and Hal is chlorine, bromine or iodine, hydrolysing, for example by mild acid catalysis, a group of the formula —C(=NH)—$R_1$ which is first formed, and hydrolysing the acetalised formyl group, for example by acid catalysis.

Other starting materials of the formula III can be prepared starting from the corresponding 1,2-phenylenediamines, which are substituted by the acyl radical of the formula —C(=O)—$R_1$ and can contain further substituents and which are accessible from the corresponding nitroanilino compounds by reduction of the nitro group, for example by hydrogen in the presence of Raney nickel, in a manner analogous to that described for the treatment of these compounds with optionally etherified glycollic acid or a suitable reactive derivative thereof, for example by reaction with mono-lower alkoxy-acetic acid or a lower alkyl ester thereof.

Furthermore, starting materials of the formula III in which $X_3$ represents formyl can also be obtained by reacting a benzimidazole which is unsubstituted in the 1-position and 2-position, contains the acyl group of the formula $R_1$—C(=O)— in the carbocyclic ring and can contain further substituents, with 2-chloro-1,1,2-trifluoro-ethene and reacting the 1-(2-chloro-1,1,2-trifluoro-ethyl)-benzimidazole, which is thus obtainable and is unsubstituted in the 2-position, contains the group of the formula $R_1$—C(=O)— in the carbocyclic part and can contain other substituents, with an alcohol, such as a lower alkanol, for example ethanol, in the presence of a base, such as an alkali metal hydroxide, for example sodium hydroxide, or with a hydroxylamine acid addition salt, for example the hydrochloride, in the presence of a base, for example pyridine. This gives a compound of the formula III in which $X_3$ is an acetalised formyl group, such as di-lower alkoxy-methyl, for example diethoxymethyl, or is the hydroxyiminomethyl group, which groups can be converted in a manner which is known per se, for example by hydrolysis, into the formyl group $X_3$.

The novel compounds in which R is a free, esterified or amidated carboxyl group or a free or etherified hydroxymethyl group can also be prepared by oxidising the group of the formula $R_1$—CH(OH)— in a corresponding compound of the formula

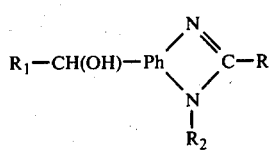 (IV)

or a salt thereof, to the desired group of the formula $R_1$—C(=O)— and, if appropriate, oxidising a free or esterified hydroxymethyl group to carboxyl and, if desired, converting a compound of the formula I, which is thus obtainable, into another compound of the formula I and/or, if desired, converting a resulting salt into the free compound or into another salt and/or converting a free salt-forming compound into a salt.

The oxidation of the $R_1$—CH(OH)— group, which can also be formed in situ in the course of the oxidation reaction, for example from the corresponding group of the formula $R_1$—$CH_2$—, or can be set free from one of its derivatives, such as an ester, for example a hydrogen halide acid ester or lower alkanoic acid ester, is effected in the customary manner. Oxidising agents which can be used are, for example, oxidising heavy metal compounds, preferably oxidising compounds containing chromium-VI and managanese-VII. The reaction is advantageously carried out in the presence of a suitable solvent or diluent, for example of acetone or pyridine, or of a mixture thereof, preferably an aqueous mixture thereof, if necessary with cooling or warming, for example in a temperature range of from about 0° C. to about 80° C.

The compounds of the formula IV which are to be used as starting materials can be prepared, for example, by acylating a corresponding chlorobenzene of the formula H—PhH—Cl in a manner which is known per se by reaction with a compound of the formula $R_1$—COHal or $(R_1CO)_2O$ in the presence of aluminium trichloride, nitrating the compound of the formula $R_1$—CO—PhH—Cl, which is thus obtainable, with nitric acid/sulphuric acid and reacting the chloronitro compound of the formula $R_1$—CO—Ph(Cl)—$NO_2$, which is thus obtainable, with ammonia or an amine of the formula $R_2NH_2$ and reducing a corresponding compound of the formula $R_1$—C(=O)—Ph($NHR_2$)—$NO_2$, which is thus obtainable, under mild conditions, for example with hydrogen in the presence of palladium-on-charcoal, advantageously in an inert solvent, such as dioxane, and under normal temperature and pressure conditions, and subjecting the compound of the formula $R_1$—CH(OH)—Ph($NHR_2$)—$NH_2$, which is thus obtainable, to a condensation reaction with an acid of the formula R—COOH or a suitable functional derivative thereof, for example with glycollic acid. The compounds of the formula

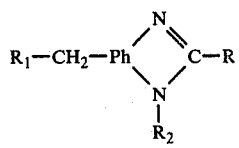 (IVa)

which have been mentioned can also be prepared in an analogous manner by reducing the nitroacyl intermediate of the formula $R_1$—C(=O)—Ph($NHR_2$)—$NO_2$ in a customary manner, for example with zinc in acetic acid, to the corresponding compound of the formula $R_1$—$CH_2$—Ph($NHR_2$)—$NH_2$ and further reacting this compound in the indicated manner.

A compound of the formula I which is obtainable according to the invention can be converted into another compound of the formula I in a manner which is known per se.

Thus, in a compound of the formula I in which R is carboxyl, this group can be converted into an esterified carboxyl group by esterification processes which are known per se. Thus, for example, the esterification can be carried out by treatment with a suitable diazo compound, such as a diazo-lower alkane, with a suitable N,N-di-lower alkylformamide acetal, for example N,N-dimethylformamide diethyl acetal, or N,N-dimethylformamide methosulphate, or an oxonium salt, such as with a tri-lower alkyl-oxonium tetrafluoborate or a tri-lower alkyloxonium hexafluorophosphate, with a carbonate or pyrocarbonate, for example with diethyl (pyro)carbonate, or with an organic sulphite or phosphite, such as a di-lower alkyl sulphite or tri-lower alkyl phosphite, in the presence of a suitable acid agent, such as p-toluenesulphonic acid, or with an alcohol in the presence of a suitable condensing agent, such as a dehydrating agent, for example dicyclohexylcarbodiimide, or, in order to form a hydroxy-lower alkyl group, with an epoxy-lower alkane, for example ethylene oxide. Furthermore, it is possible to react a compound of the formula I, in which a free carboxyl group R is in the form of a salt, for example in the form of an alkali metal salt, such as the sodium salt, with a reactive ester of an alcohol, for example with a strong acid, such as a corresponding halide, for example chloride, bromide or iodide, or disubstituted sulphate, or to react a compound of the formula I in which a free carboxyl group R is in the anhydride form, preferably in the form of a halogenocarbonyl group, for example a chlorocarbonyl group, which can be formed, for example, by treating a compound of the formula I in which R represents carboxyl with a halogenating agent, for example thionyl chloride, with a metal alcoholate or an alcohol in the presence of an acid-binding base and thus to obtain a compound of the formula I in which R is esterified carboxyl. It is possible for any substituents which may be present in an esterifying reagent to be in the functionally modified form and then, in a compound of the formula I in which R, for example, is substituted lower alkoxycarbonyl, in which substituents are in the functionally modified form, for these substituents to be set free. Thus, for example, 2,3-epoxy-propyl chloride can be used as the esterifying reagent and a 2,3-epoxy-propoxy grouping R in the resulting ester can subsequently be hydrolysed to the desired 2,3-dihydroxypropoxy grouping.

In a compound of the formula I in which R is esterified carboxyl, for example including p-nitro- or 2,4-dinitro-phenoxy-or-benzyloxy-carbonyl, this group can be converted by trans-esterification, for example by treatment with an alcohol, if necessary in the presence of a suitable trans-esterification catalyst, such as a substituted or unsubstituted alkali metal alkanolate, for example a sodium alkanolate or potassium alkanolate, into another esterified carboxyl group.

In a resulting compound of the formula I in which R is free carboxyl, carboxyl in the form of an anhydride or esterified carboxyl, this group can also be converted in a manner which is known per se into substituted or unsubstituted carbamyl. Thus, a compound of the formula I in which a carboxyl group R is in the form of an anhydride, especially in the form of a halogenocarbonyl group, for example a chlorocarbonyl group, or in the esterified form can be treated with ammonia, hydroxylamine or a primary or secondary amine and compounds of the formula I in which R is substituted or unsubstituted carbamyl can thus be obtained. Furthermore, the ammonium salt or an amine salt of a compound of the formula I in which R is carboxyl can be converted by dehydration with a suitable dehydrating agent, such as sulphuric acid, into a compound of the formula I in which R is substituted or unsubstituted carbamyl.

The compounds mentioned, in which R is carboxyl in the form of a halide, can be prepared starting from compounds of the formula I in which R is carboxyl by treatment with a thionyl halide, such as thionyl chloride. If $R_2$ is hydrogen these compounds can dimerise to compounds of the formula

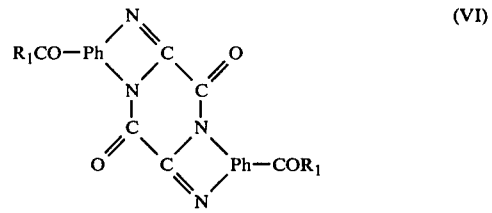

An intermediate of this type can be converted into a compound of the formula I in which R is esterified carboxyl or substituted or unsubstituted carbamyl by, for example, treatment with a suitable alcoholate, such as an alkali metal alcoholate, for example a sodium or potassium alcoholate, or with an alcohol in the presence of a mineral acid, for example hydrogen chloride, or with ammonia, hydroxylamine or a primary or secondary amine.

An esterified carboxyl group or a substituted or unsubstituted carbamyl group R in a compound of the formula I can be converted into the free carboxyl group in a customary manner, for example by hydrolysis, usually in an alkaline medium, such as by treatment with water in the presence of an alkali metal hydroxide or alkaline earth metal hydroxide, for example sodium hydroxide.

In a compound of the formula I in which $R_2$ is hydrogen this can be replaced by an aliphatic radical, for example by treatment with a reactive ester of a corresponding alcohol, such as a halide, in the presence of a base, for example of an alkali metal alcoholate.

A carboxyl group R, which can be free or in the form of a halide or salt, can, furthermore, be reduced to hydroxymethyl by reaction with a borohydride or with hydrogen in the presence of a hydrogenation catalyst. A borane, for example diborane or the borane-tetrahydrofurane complex, is preferably used for the reduction of a carboxyl group which can be in the form of a salt, for example in the form of an alkali metal salt, such as the sodium salt. Halogenocarbonyl groups, such as chlorocarbonyl, are preferably reduced with hydrogen in the presence of palladium, preferably on a support, such as barium sulphate, and if necessary of a sulphur-containing co-catalyst, for example of thiourea.

Furthermore, in a compound of the formula I in which R represents hydroxymethyl, this can be converted into an etherified hydroxymethyl group in a customary manner, for example by reaction with an etherifying agent. Etherifying agents are, for example, reactive esters of corresponding alcohols, for example esters thereof with an inorganic acid, such as hydrochloric acid, hydrobromic acid or hydriodic acid or sulphuric acid, or with organic sulphonic acids, for example with methanesulphonic acid, benzenesulphonic acid, p-bromobenzenesulphonic acid or p-toluenesulphonic acid, and also epoxides derived from corresponding 1,2-diols. The reaction with the said etherifying agents can be carried out in a customary manner, for example in the presence of an alkali metal hydride or alkali metal alcoholate, for example of sodium hydride or sodium methylate, or by employing the compound to be etherified in the form of a salt, for example the sodium salt. Furthermore, in a compound of the formula I in which R is hydroxymethyl, this can be esterified in a customary manner, for example converted into an esterified hydroxymethyl group R by direct esterification with a corresponding carboxylic acid in the presence of a mineral acid, for example of hydrochloric acid or sulphuric acid, or by reaction with a reactive derivative, for example an anhydride, such as the anhydride or chloride, or an ester, such as a lower alkyl ester or p-nitrophenyl or 2,4-dinitrophenyl ester, of the carboxylic acid, if necessary in the presence of an acid or, in particular, basic condensing agent, for example of pyridine in the case of the reaction with an acid anhydride and, for example, of an alkali metal alcoholate, such as a sodium or potassium alcoholate, in the case of the reaction with an ester. However, the etherification or esterification of a hydroxymethyl group can also be carried out by first converting this into a halogenomethyl group in a customary manner, for example using phosphorus tribromide or thionyl chloride, and subsequently reacting this group with an alkali metal alcoholate, for example the sodium alcoholate, of the corresponding alcohol or an alkali metal salt, for example the sodium salt, of the corresponding carboxylic acid.

Free or esterified hydroxymethyl groups R can also be oxidised to carboxyl groups and etherified hydroxymethyl groups can be oxidised to esterified carboxyl groups. The oxidation can be carried out in a manner which is known per se, for example by reaction with an oxidising heavy metal compound, preferably with an oxidising compound containing chromium-VI or manganese-VII, for example with chromium trioxide or, especially, potassium permanganate, when starting from hydroxymethyl, and also with a compound containing manganese-IV, such as manganese dioxide, when starting from etherified hydroxymethyl R. The reaction is preferably carried out in the presence of a suitable solvent or diluent, for example of acetone or pyridine, or of a mixture thereof, preferably an aqueous mixture thereof, if necessary with cooling or warming, for example in a temperature range of from about 0° C. to about 80° C.

Resulting free compounds of the formula I in which R is carboxyl can be converted into salts in a manner which is known per se, inter alia by treatment with a base or with a suitable salt of a carboxylic acid, usually in the presence of a solvent or diluent.

Resulting salts can be converted into the free compounds in a manner which is known per se, for example by treatment with an acid reagent, such as a mineral acid.

The compounds, including their salts, can also be obtained in the form of their hydrates or can incorporate the solvent used for crystallisation.

Because of the close relationship between the novel compounds in the free form and in the form of their salts, the free compounds or their salts, in the preceding and following text, are, where appropriate, also to be understood as meaning the corresponding salts or free compounds in respect of general sense and intended use.

The invention also relates to those embodiments of the process in which a compound obtainable as an intermediate at any stage of the process is used as the starting material and the missing process steps are carried out, or a starting material is formed under the reaction conditions or is used in the form of a derivative thereof, if appropriate in the form of a salt.

The starting materials used in the process of the present invention are preferably those which lead to the compounds described initially as being particularly valuable.

The present invention also relates to pharmaceutical formulations which contain compounds of the formula I or salts thereof which can be used pharmaceutically. The pharmaceutical formulations according to the invention are those for enteral, such as oral, nasal or rectal, and also parenteral administration or topical application to warm-blooded animals and contain the pharmacological active compound on its own or together with an excipient which can be used pharmaceutically. The dosage of the active compound depends on the species of warm-blooded animal, the age and the state of health of the individual and also on the mode of administration.

The novel pharmaceutical formulations contain, for example, up to about 95%, and preferably from about 5% to about 90%, of the active compound. Pharmaceutical formulations according to the invention are, for example, those in the form of dosage units, such as dragees, tablets, capsules or suppositories, as well as ampoules and also inhalation formulations and also pharmaceutical formulations which can be used topically and locally (for example for insufflation).

The pharmaceutical formulations of the present invention are prepared in a manner which is known per se, for example by means of conventional mixing, granulating, dragee-making, dissolving or lyophilising processes. Thus, pharmaceutical formulations for oral use can be obtained by combining the active compound with solid excipients, granulating a resulting mixture if desired and processing the mixture or granules, after adding suitable auxiliaries if desired or necessary, to give tablets or dragee cores.

Suitable excipients are, especially, fillers, such as sugars, for example lactose or sucrose, mannitol or sorbitol, cellulose formulations and/or calcium phosphates, for example tricalcium phosphate or calcium hydrogen phosphate, as well as binders, such as starch paste using, for example, maize starch, wheat starch, rice starch or potato starch, gelatine, tragacanth, methylcellulose and/or polyvinylpyrrolidone, and/or, if desired, disintegrating agents, such as the abovementioned starches, and also carboxymethyl-starch, cross-linked polyvinylpyrrolidone, agar or alginic acid or a salt thereof, such as sodium alginate. Auxiliaries are, in particular, flow control agents and lubricants, for example silica, talc, stearic acid or salts thereof, such as magnesium stearate or calcium stearate, and/or polyethylene glycol. Dragee cores are provided with suitable coatings which, if desired, are resistant to gastric juices, and for this purpose, inter alia, concentrated sugar solutions, which can contain gum arabic, talc, polyvinylpyrrolidone, polyethylene glycol and/or titanium dioxide, lacquer solutions in suitable organic solvents or solvent mixtures or, in order to produce coatings resistant to gastric juices, solutions of suitable cellulose formulations, such as acetylcellulose phthalate or hydroxypropylmethylcellulose phthalate, are used. Dyestuffs or pigments can be added to the tablets or dragee coatings, for example for identification or in order to characterise different active compound doses.

Other pharmaceutical formulations which can be used orally are push-fit capsules made of gelatine, as well as soft, sealed capsules made of gelatine and a plasticiser, such as glycerol or sorbitol. The push-fit capsules can contain the active compound in the form of granules, for example mixed with fillers, such as lactose, binders, such as starches, and/or lubricants, such as talc or magnesium stearate, and can contain stabilisers. In soft capsules, the active compound is preferably dissolved or suspended in suitable liquids, such as fatty oils, liquid paraffin or liquid polyethylene glycols, it also being possible to add stabilisers.

Possible pharmaceutical formulations which can be used rectally are, for example, suppositories, which consist of a combination of the active compound with a suppository base. Suitable suppository bases are, for example, natural or synthetic triglycerides, paraffin hydrocarbons, polyethylene glycols or higher alkanols. In addition it is also possible to use gelatine rectal capsules which contain a combination of the active compound with a base; bases which can be used are, for example, liquid triglycerides, polyethylene glycols or paraffin hydrocarbons.

Formulations suitable for parenteral administration are, in particular, aqueous solutions of an active compound in the water-soluble form, for example of a water-soluble salt, and also suspensions of the active compound, such as corresponding oily injection suspensions, in which case suitable lipophilic solvents or vehicles, such as fatty oils, for example sesame oil, or synthetic fatty acid esters, for example ethyl oleate or triglycerides, are used, or aqueous injection suspensions which contain substances which increase the viscosity, for example sodium carboxymethylcellulose, sorbitol and/or dextran, and can also contain stabilisers.

Inhalation formulations for the treatment of the respiratory passages by nasal or buccal administration are, for example, aerosols or sprays which can disperse the pharmacological active compound in the form of a powder or in the form of drops of a solution or suspension. Formulations which have powder-dispersing properties usually contain, in addition to the active compound, a liquid propellant gas which has a boiling point below room temperature and also, if desired, excipients, such as liquid or solid non-ionic or anionic surface-active agents and/or solid diluents. Formulations in which the pharmacological active compound is in solution contain, in addition to this active compound, a suitable propellant and also, if necessary, an additional solvent and/or a stabiliser. In place of the propellant gas, it is also possible to use compressed air and this can be produced as required by means of a suitable compression and pressure release device.

Pharmaceutical formulations for topical and local use are, for example, lotions and creams which contain a liquid or semi-solid oil-in-water or water-in-oil emulsion, and ointments (such formulations preferably containing a preservative) for the treatment of the skin, eye drops which contain the active compound in aqueous or oily solution and eye ointments, which are preferably prepared in a sterile form, for the treatment of the eyes, powders, aerosols and sprays (similar to those described above for the treatment of the respiratory passages) and also coarse powders, which are administered through the nostrils by rapid inhalation, and nose drops, which contain the active compound in aqueous or oily solution, for the treatment of the nose or lozenges, which contain the active compound in a composition generally consisting of sugar and gum arabic or tragacanth, to which flavourings can be added, as well as pastilles, which contain the active compound in an inert composition, for example consisting of gelatine and glycerol or sugar and gum arabic, for the local treatment of the mouth.

The invention also relates to the use of the novel compounds of the formula I, or salts thereof, as pharmacologically active compounds and especially as antiallergic agents, preferably in the form of pharmaceutical formulations. The daily dose which is administered to a warm-blooded animal weighing about 70 kg is from about 2 mg to about 7,000 mg, depending on the form of administration.

The examples which follow illustrate the invention described above; however, they are not intended to restrict the scope of the invention in any way. Temperatures are given in degrees Centigrade.

EXAMPLE 1

A mixture of 44.6 g of crude 4,5-diamino-2-methyl-butyrophenone and 23 g of glycollic acid is heated, under a nitrogen atmosphere, to an internal temperature of 130° and kept at this temperature for 2½ hours. The brown-black reaction mass is cooled to room temperature and dissolved in about 300 ml of 2 N hydrochloric acid; the brown solution, which contains flocculated material, is treated with an active charcoal formulation and filtered through a diatomaceous earth formulation (Hyflo). The pH of the clear brown filtrate is adjusted to 9 by adding an aqueous concentrated solution of sodium hydroxide. The mixture is cooled in an ice bath and the crystalline precipitate is filtered off, washed with water and dried under 100 mm Hg and at 50° for 6 hours. The product is dissolved in 100 ml of hot ethanol, the solution is treated with an active charcoal formulation and filtered and the filtrate is diluted with 100 ml of water. 5-Butyryl-6-methyl-benzimidazole-2-methanol, which is thus obtainable, is filtered off and washed with water and di ether; melting point 176°–178°.

The starting material can be obtained as follows:

A yellow suspension of 900 ml of 3-chloro-toluene and 367.5 g of aluminium chloride (finely powdered) is treated with 266 g of butyryl chloride in the course of one hour. Hydrogen chloride gas evolves during the dropwise addition; the reaction is exothermic (the temperature is allowed to rise to 70°) and the aluminium chloride dissolves. After the addition of the butyryl chloride is complete, the reaction mixture is kept at 70° until the evolution of gas has ceased (about 45 minutes) and is then cooled to 50° and poured onto 2,500 g of ice.

In each case, two identical batches are taken together and extracted with ethyl acetate; the organic extract is washed twice with 2 N hydrochloric acid, once with a saturated aqueous solution of sodium chloride, twice with a 2 N aqueous solution of sodium carbonate and once with a saturated aqueous solution of sodium chloride, dried and evaporated. The brown, oily residue which is thus obtainable is distilled; a mixture of 4-chloro-2-methyl-butyrophenone and 2-chloro-4-methyl-butyrophenone is obtained at 160°–163°/14 mm Hg.

Concentrated sulphuric acid (1,275 ml), which has been cooled to −20° to −25° by means of a carbon dioxide/chloroform mixture, is treated dropwise, while stirring well, with 285.5 g of the mixture of 4-chloro-2-methyl-butyrophenone and 2-chloro-4-methyl-butyrophenone in the course of 10 minutes. The resulting solution is treated at −20° to −25° in the course of 30 minutes with a mixture of 240 ml of concentrated sulphuric acid and 75 ml of 100% strength nitric acid (d:1.52) and the mixture is then stirred for a further 15 minutes, during which time the temperature is allowed to rise to −15°. The mixture is poured into 8,000 ml of ice water; the oil which has separated out is extracted with chloroform. The organic extract is washed once with an aqueous solution of sodium bicarbonate and once with water, dried over sodium sulphate and evaporated. The residue is dissolved in twice the amount of hot methanol and the solution is left to stand for 16 hours. The crystalline precipitate is filtered off, washed with cold water and dried under 100 mm Hg and at room temperature for 18 hours. This gives 4-chloro-2-methyl-5-nitro-butyrophenone which melts at 71°–72°.

A solution of 120.7 g of 4-chloro-2-methyl-5-nitrobutyrophenone in 250 ml of dimethylsulphoxide is warmed to a temperature of 95°–100°, a vigorous stream of ammonia already being passed through the solution during the heating period. The solution is treated with ammonia gas for a further 18 hours at a temperature of 95°–100° and is then cooled and poured into about 5,000 ml of an ice/water mixture. The product starts to precipitate as a resin but crystallises on stirring. The mixture is filtered; the coarse product is then ground and washed with water and then dissolved in about 1,000 ml of ethyl acetate. The solution is dried over sodium sulphate and evaporated. The residue is dissolved in 245 ml of hot benzene and the solution is treated with an active charcoal formulation and filtered; the filtrate is diluted with 490 ml of petroleum ether and the crystalline 4-amino-2-methyl-5-nitro-butyrophenone is filtered off; melting point 90°–92°.

A solution of 66.6 g of 4-amino-2-methyl-5-nitrobutyrophenone in 600 ml of dioxane and 150 ml of water is heated under reflux, while stirring, and treated dropwise, in the course of 15 minutes, with a solution of 240 g of sodium dithionite in 1,050 ml of water. The reaction mixture is boiled for a further 15 minutes and then treated dropwise, in the course of 30 minutes, with 150 ml of concentrated hydrochloric acid; during this treatment a pH value of 3 is reached and a fairly large amount of sulphur dioxide is formed. The organic solvent is evaporated; the residue is rendered alkaline with an aqueous solution of sodium hydroxide and extracted with chloroform. The organic extract is washed twice with water, dried over sodium sulphate and evaporated. 4,5-Diamino-2-methyl-butyrophenone of melting point 84°–87°, which is thus obtainable, is used without further purification.

EXAMPLE 2

The conversion of 4-chloro-2-methyl-5-nitro-butyrophenone into 4,5-diamino-2-methyl-butyrophenone can, however, also be carried out in the following way and in this case also a crude mixture of isomers can be used as the starting material.

24.5 g of crude chloro-methyl-nitro-butyrophenone (containing about 75% of 4-chloro-2-methyl-5-nitrobutyrophenone) are dissolved in 300 ml of ethanol and the solution is transferred to an autoclave. 50 g of ammonia are then injected and the mixture is heated at 100° for 12 hours. The mixture is evaporated to dryness under reduced pressure, the residue is treated with 200 ml of 2 N hydrochloric acid and the resulting mixture is heated at 80°–90° for one hour, cooled to 10°–15° by adding ice and filtered. The residue is dissolved in methylene chloride, dried over sodium sulphate and evaporated, with the addition of cyclohexane at the end. The crystalline 4-amino-2-methyl-5-nitro-butyrophenone is filtered off and washed with petroleum ether. It melts at 92°–95°.

66.7 g of 4-amino-2-methyl-5-nitro-butyrophenone are dissolved in 900 ml of methanol, treated with 7 g of Raney nickel and hydrogenated at 20°–25° under normal pressure. After 19.6 liters of hydrogen have been taken up, the hydrogenation is discontinued, the catalyst is filtered off, the filtrate is treated with 100 ml of concentrated hydrochloric acid and the methanol is stripped off under reduced pressure. The 4,5-diamino-2-methyl-butyrophenone hydrochloride, which is now crystalline, is filtered off, washed with ethanol/ether and dried. It melts at above 160° with partial decomposition.

EXAMPLE 3

A suspension of 2.95 g of 5-butyryl-6-methyl-benzimidazol-2-yl-methanol in 180 ml of acetone is diluted with 140 ml of water and a solution forms on stirring. This solution is treated, at room temperature, with 2.95 g of potassium permanganate, which is added all at once, and stirred for a further one hour at room temperature, during which time the violet coloration of the oxidising agent disappears and the brown-black sludge of manganese dioxide separates out. The acetone is evaporated under reduced pressure and the resulting suspension is filtered with the aid of a diatomaceous earth formulation (Hyflo) and the material on the filter is washed with water. The pH of the filtrate is adjusted to 3 to 3.5 with acetic acid; the resulting flocculent precipitate is filtered off, washed with water and dried at 35°. 5-Butyryl-6-methyl-benzimidazole-2-carboxylic acid, which is thus obtainable, melts at 127°–137°, depending on the rate of heating and with decomposition.

The sodium salt of 5-butyryl-6-methyl-benzimidazole-2-carboxylic acid can be obtained by lyophilising a solution of the free acid in an aqueous solution of the equivalent amount of sodium hydroxide.

EXAMPLE 4

A mixture of 9.8 g of 5-amino-2-methyl-4-methylaminobutyrophenone and 4.15 g of glycollic acid is heated in an oil bath at 130°. After 150 minutes the reaction product, together with the product from a second batch of 3 g of 5-amino-2-methyl-4-methylamino-butyrophenone and 1.27 g of glycollic acid, is taken up in 300 ml of 2 N hydrochloric acid and the mixture is filtered. The filtrate is rendered alkaline; the oil which has separated out is extracted with three portions of ethyl acetate, the organic extract is washed twice with water, dried and filtered and the filtrate is evaporated. The brown, oily residue crystallises spontaneously and is recrystallised from ethyl acetate. 5-Butyryl-1,6-dimethyl-benzimidazole-2-methanol, which is thus obtainable, melts at 141.5°–142.5°.

The starting material can be prepared as follows:

A mixture of 24.1 g of 4-chloro-2-methyl-5-nitrobutyrophenone and 250 ml of a 33% strength solution of methylamine in ethanol is left to stand at room temperature; the crystalline starting material dissolves slowly and a yellow coloration develops. The reaction is slightly exothermic; the mixture is therefore cooled using a water bath in order to prevent too much methylamine escaping. After 20 minutes everything has dissolved and a precipitate then starts to separate out. The mixture is left to stand for 16 hours at room temperature and is then evaporated to dryness under reduced pressure. The residue is treated with diethyl ether (about 1,000 ml), ice and sodium carbonate, the mixture is shaken thoroughly and the organic layer is separated off. This layer is washed twice with water and the aqueous solution is back-washed with diethyl ether. The combined organic solutions are dried over sodium sulphate and filtered and the filtrate is evaporated to a volume of about 300 ml, then diluted with 100 ml of petroleum ether and cooled. Yellow, crystalline 2-methyl-4-methylamino-5-nitro-butyrophenone precipitates and is filtered off, washed with petroleum ether and dried in air; melting point 107°–108°.

A solution of 4.7 g of 2-methyl-4-methylamino-4-nitrobutyrophenone in 40 ml of dioxane is diluted with water and heated to the reflux temperature and then treated, in the course of 10 minutes, with a solution of 16 g of sodium dithionite in 70 ml of water, whereupon the yellow colour of the reaction mixture pales. The mixture is boiled under reflux for a further 15 minutes, the pH value is adjusted to 3 by adding about 30 ml of 6 N hydrochloric acid and the mixture is boiled for a further 15 minutes under reflux, during which time the sulphur dioxide escapes. The pH value of the reaction mixture is adjusted to 2, the mixture is boiled under reflux for about a further 5 minutes and the dioxane is then evaporated under reduced pressure. The hydrochloride of 5-amino-2-methyl-4-methylamino-butyrophenone precipitates from the residual solution; the suspension is cooled, rendered alkaline with a concentrated aqueous solution of sodium hydroxide and extracted with chloroform. The organic extract is washed twice with water, dried, filtered and evaporated. 5-Amino-2-methyl-4-methylamino-butyrophenone melts at 126°–128°.

EXAMPLE 5

The conversion of 4-chloro-2-methyl-5-nitro-butyrophenone into 4-amino-2-methyl-5-methylamino-butyrophenone can also be carried out in the following way and a crude mixture of isomers can also be used as the starting material.

241 g of crude chloro-methyl-nitrobutyrophenone (containing about 75% of 4-chloro-2-methyl-5-nitro-butyrophenone) are suspended in 1,200 ml of ethanol and the suspension is treated with 1,200 ml of 33% strength methylamine solution, whereupon a solution forms, an exothermic reaction taking place. The solution is left to stand for 2 days and is evaporated to dryness under reduced pressure, the residue is treated with 600 ml of 2 N hydrochloric acid and the mixture is warmed at 80°–90° for 1 hour. It is cooled to about 15° by adding ice and the crystalline precipitate is filtered off, washed with water and taken up in methylene chloride, the solution is dried over sodium sulphate and the methylene chloride is evaporated under reduced pressure, finally with the addition of cyclohexane and petroleum ether (boiling range 60°–80°), the residue is cooled and 2-methyl-4-methylamino-5-nitrobutyrophenone with a melting point of 105°–107° is filtered off.

59.1 g of 2-methyl-4-methylamino-5-nitro-butyrophenone are dissolved in 1,000 ml of methanol, treated with 6 g of Raney nickel and hydrogenated at 20°–25° under normal pressure. After 16.8 liters of hydrogen have been taken up, the hydrogenation is discontinued, the mixture is warmed gently to dissolve the material which has precipitated, the catalyst is filtered off and the filtrate is treated with 50 ml of concentrated hydrochloric acid, cooled to 3° and filtered. This gives 4-amino-2-methyl-5-methylamino-butyrophenone hydrochloride with a melting point above 180° (decomposition).

EXAMPLE 6

A solution of 1.23 g of 5-butyryl-1,6-dimethyl-benzimidazole-2-methanol in 75 ml of acetone and 25 ml of water is treated, while stirring, with 1.2 g of potassium permanganate, which is added all at once. After an initially weakly exothermic reaction, manganese dioxide begins to precipitate after 30 minutes. After four hours the reaction mixture is treated with a small amount of isopropanol and the organic solvent is then evaporated under reduced pressure. The residual aqueous suspension is filtered through a diatomaceous earth formulation (Hyflo). The turbid filtrate is extracted twice with chloroform and the organic extract is discarded. The aqueous phase is freed from the final traces of chloroform under reduced pressure and then treated with an active charcoal formulation and filtered. The pH of the filtrate is adjusted to 3–4 with acetic acid and 5-butyryl-1,6-dimethylbenzimidazole-2-carboxylic acid then starts to precipitate in the form of fine needles. The mixtue is cooled and the precipitate is filtered off, washed with water and diethyl ether and dried at room temperature under a high vacuum; melting point above 110° (decomposition). The sodium salt melts at 275°–280° (from aqueous acetone).

EXAMPLE 7

A mixture of 2.9 g of 3,4-diamino-valerophenone and 1.5 g of glycollic acid is heated at 130° for 2 hours under a nitrogen atmosphere. After cooling, the reaction product is taken up in 2 N hydrochloric acid; the solution is treated with an active charcoal formulation and filtered through a diatomaceous earth formulation (Hyflo) and the filtrate is rendered alkaline by adding a concentrated aqueous solution of sodium hydroxide. The crystalline precipitate is filtered off, washed with water and diethyl ether and dried. 5(6)-Valeryl-benzimidazole-2-methanol, which is thus obtainable, melts at 134°–136°.

The starting material can be prepared as follows:

A mixture of 346 ml of chlorobenzene and 120 g of valeryl chloride is treated, at room temperature, in the course of 1 hour with portions of aluminium chloride and the mixture is at the same time heated to 70°. The mixture is stirred for a further hour at this temperature and then cooled to 25° and the dark red reaction mixture is poured on to 1,000 g of ice. Concentrated hydrochloric acid is added and the mixture is then extracted with ethyl acetate. The organic extract is washed with 2 N hydrochloric acid, filtered through a diatomaceous earth formulation (Hyflo) and washed with further 2 N hydrochloric acid, twice with water, with a 2 N aqueous solution of sodium carbonate and with water. It is dried over sodium sulphate and filtered and the filtrate is evaporated under reduced pressure. The residue is distilled; 4-chloro-valerophenone is obtained at 155°–156°/14 mm Hg; the product crystallises and melts at 28°–30°.

50 ml of concentrated sulphuric acid are treated, while stirring, with 9.9 g of 4-chloro-valerophenone, while cooling with an ice/sodium chloride mixture. The bulk of the product dissolves, a slightly exothermic reaction taking place, and a yellow suspension forms, which is treated, while stirring vigorously and at a temperature of $-10°$ to $-5°$, with a mixture of 20 ml of concentrated sulphur acid and 10.4 ml of concentrated nitric acid (d = 1.52), in the course of 10 minutes. After a reaction time of five minutes, the mixture is poured onto ice and the aqueous mixture is extracted with chloroform. The organic extract is washed once with an aqueous solution of sodium carbonate and with water, dried over sodium sulphate and filtered through silica gel. 4-Chloro-3-nitro-valerophenone is obtained as an oily residue after evaporating the filtrate.

Gaseous ammonia is passed through a solution of 18.1 g of 4-chloro-3-nitro-valerophenone in 40 ml of dimethylsulphoxide at room temperature. A yellow coloration develops immediately and the solution warms to above 40°. After 105 minutes (final temperature: 32°), the reaction mixture is heated, while continuing to pass in ammonia, to 70°, kept at this temperature for two hours and then heated at 95° for a further two hours. After cooling, the mixture is poured into about 400 ml of water and the resulting mixture is then acidified with concentrated hydrochloric acid and, after a few minutes, rendered alkaline again using concentrated aqueous ammonia solution. The yellow crystalline precipitate is filtered off; the moist crystals are taken up in ethyl acetate, the solution is dried over sodium sulphate and filtered and the filtrate is evaporated. The crystalline residue is dissolved in hot benzene and the solution is treated with silica gel and filtered. The filtrate, which is still brown, is diluted with petroleum ether and the hot mixture is again treated with silica gel and filtered. The filtrate is diluted with petroleum ether; 4-amino-3-nitro-valerophenone crystallises out and is filtered off; melting point 115°-117°.

A suspension of 3.9 g of 4-amino-3-nitro-valerophenone in 35 ml of dioxane and 9 ml of water is heated to the reflux temperature and the resulting solution is treated, in the course of 10 minutes, while boiling, with 14 g of sodium dithionite in 60 ml of water. The reaction mixture is boiled under reflux for a further 15 minutes and 6 N hydrochloric acid is then added dropwise until the pH is 3, a little sulphur dioxide escaping. The pH value is adjusted to 2, the mixture is allowed to react for a few minutes and the organic solvent is then removed under reduced pressure. The residual aqueous suspension is rendered alkaline in the cold and extracted with 5 50 ml portions of chloroform. The combined organic extracts are washed twice with water, dried and filtered and the filtrate is evaporated. 3,4-Diamino-valerophenone is obtained in the form of brown crystals; melting point 106°-107°.

EXAMPLE 8

A solution of 1.15 g of 5(6)-valeryl-benzimidazole-2-methanol in 75 ml of acetone and 55 ml of water is heated with 1.15 g of potassium permanganate, which is added all at once, and the mixture is stirred at room temperature for one hour. After 5 minutes manganese dioxide begins to precipitate and after 30 minutes the violet colour has disappeared. The acetone is evaporated under reduced pressure; the residual mixture is filtered through a diatomaceous earth formulation (Hyflo) and the filter residue is washed with water. The filtrate is acidified to pH 4 with acetic acid; the resulting precipitate is filtered off, washed with water and dried at room temperature. 5(6)-Valeryl-benzimidazole-2-carboxylic acid, which is then obtainable, melts at 145° (with decomposition).

EXAMPLE 9

It is possible to prepare the following compounds inter alia, in a manner analogous to that described in Examples 1, 2, 4, 5, 7 and 8.

5-Acetyl-6-methyl-benzimidazole-2-carboxylic acid; 6-methyl-5-propionyl-benzimidazole-2-carboxylic acid; 6-methyl-5-valeryl-benzimidazole-2-carboxylic acid; 5(6)-butyrylbenzimidazole-2-carboxylic acid; 5-butyryl-6-methoxy-benzimidazole-2-carboxylic acid; 5-butyryl-6-chloro-benzimidazole-2-carboxylic acid; 5-cyclopropylcarbonyl-6-methyl-benzimidazole-2-carboxylic acid; 5-cyclohexylcarbonyl-6-methyl-benzimidazole-2-carboxylic acid; 5-(4-methoxy-butyryl)-6-methyl-benzimidazole-2-carboxylic acid; 6-methyl-5-(4-methylthiobutyryl)-benzimidazole-2-carboxylic acid; 6-methyl-5-(4-methylsulphinyl-butyryl)-benzimidazole-2-carboxylic acid; 6-methyl-5-(4-phenylthio-butyryl)-benzimidazole-2-carboxylic acid; 6-methyl-5-(4-phenylsulphinyl-butyryl)-benzimidazole-2-carboxylic acid; and methyl 5-butyryl-6-methyl-benzimidazole-2-carboxylate.

EXAMPLE 10

59.1 g of 2-methyl-4-methylamino-5-nitro-butyrophenone are dissolved in 1,000 ml of methanol, treated with 6 g of Raney nickel and hydrogenated at 20°-25° under normal pressure. After 17.2 liters of hydrogen have been taken up, the hydrogenation is discontinued and the reaction mixture is warmed gently and treated, under nitrogen, with a solution of 17.1 g of glycollic acid in 30 ml of methanol. The catalyst is filtered off, the filtrate is evaporated to dryness under reduced pressure and the residue is heated at 130° for 3 hours. After cooling, the residue is dissolved in 2 N hydrochloric acid and the solution is washed with ethyl acetate, rendered alkaline and extracted with methylene chloride. The extract is washed twice with water, concentrated to 100 ml and treated with ethyl acetate and all of the methylene chloride is stripped off. 5-Butyryl-1,6-dimethyl-benzimidazole-2-methanol with a melting point of 141.5°-142.5°, which has precipitated, is filtered off and dried in vacuo.

The starting material can be prepared as follows:

241 g of chloro-methyl-nitro-butyrophenone (containing about 75% of 4-chloro-2-methyl-5-butyrophenone) are suspended in 1,200 ml of ethanol and the suspension is treated with 1,200 ml of 33% strength methylamine solution and warmed gently. When the exothermic reaction starts, the mixture is cooled somewhat and then left to stand at room temperature for 2 days. It is evaporated to dryness under reduced pressure, the residue is treated with 600 ml of 2 N hydrochloric acid, the mixture is heated to 80°-90° for 1 hour and cooled to about 15° by adding ice and the precipitate is filtered off. It is washed with water and dissolved in methylene chloride, the solution is dried over sodium sulphate and concentrated under reduced pressure and cyclohexane is added, all of the methylene chloride is stripped off and the product is filtered off and dried in vacuo. 2-Methyl-4-methylamino-5-nitrobutyrophenone melts at 105°-107°.

EXAMPLE 11

41.5 g of 4-amino-2-methyl-5-nitro-valerophenone dissolved in 500 ml of methanol are treated with 4 g of Raney nickel and hydrogenated under normal pressure until 11.6 liters of hydrogen have been taken up. The crude hydrogenation solution, which contains the 3-methyl-4-valeryl-1,2-phenylenediamine formed, is treated, under nitrogen, with a solution of 26.6 g of glycollic acid in 100 ml of methanol and the catalyst is filtered off. The methanol is stripped off under reduced pressure and the residue is heated at 130° for 90 minutes and after cooling is treated with 400 ml of 2 N hydrochloric acid and the mixture is stirred for one hour, treated with a filter aid and filtered through diatomaceous earth. The filtrate is brought to pH 9, first with concentrated sodium hydroxide solution and then with 4 N sodium carbonate solution, and cooled, whereupon 6-methyl-5-valeryl-benzimidazole-2-methanol precipitates out. This is filtered off with suction, washed with 200 ml of ethyl acetate and dried under reduced pressure. The product melts at 169°-171°. A further product with a melting point of 168°-170° can be obtained from the ethyl acetate used for washing, by concentrating to about 50 ml.

The starting material can be prepared as follows:

302 g of valeroyl chloride are added dropwise, in the course of 120 minutes, to a stirred suspension of 367 g of aluminium trichloride in 900 ml of m-chlorotoluene. The reaction temperature should not exceed 45°; if necessary, the reaction mixture is cooled with ice water. The mixture is stirred for several hours more, poured onto 4,000 g of ice and extracted with ethyl acetate. The combined extracts are washed successively with 2 N hydrochloric acid, water, 2 N sodium carbonate solution and twice with water, dried over sodium sulphate and evaporated under reduced pressure, finally at 80°.

The residue is distilled under reduced pressure and a mixture of isomers containing about 50% of 4-chloro-2-methyl-valerophenone passes over at 150° and under 12 mm Hg.

130 ml of sulphuric acid cooled to −23° are treated dropwise, at −25° to −20°, first with the mixture of isomers containing about 50% of 4-chloro-2-methyl-valerophenone and then with a mixture of 24 ml of sulphuric acid and 7.5 ml of nitric acid with a density of 1.52. The reaction has ended after about 20 minutes. The mixture is poured on to 600 g of ice, the precipitate is filtered off with suction and taken up in chloroform and the solution is washed successively with a saturated solution of sodium carbonate and twice with water, dried over sodium sulphate and evaporated to dryness. The evaporation residue is taken up in 40 ml of methanol. A mixture of isomers containing about 50% of 4-chloro-2-methyl-5-nitro-valerophenone crystallises out on cooling. This mixture is filtered off and washed with cold methanol.

Ammonia is passed into a solution, which has been heated to 95°-100°, of 38 g of the mixture of isomers containing about 50% of 4-chloro-2-methyl-5-nitro-valerophenone, in 240 ml of dimethylsulphoxide, for about 14 hours until an intense yellow coloration has developed. The mixture is allowed to cool and is poured onto 2,000 g of ice, the resulting mixture is acidified with concentrated hydrochloric acid and rendered alkaline with sodium hydroxide solution and the precipitate is filtered off with suction, washed with water, dried at 40°, suspended in boiling cyclohexane and again filtered off with suction. This gives 4-amino-2-methyl-5-nitro-valerophenone with a melting point of 108°-112°, which is pure according to chromatography.

EXAMPLE 12

A solution of 9.85 g of 6-methyl-5-valeryl-benzimidazole-2-methanol in a mixture of 350 ml of acetone and 80 ml of water is treated with 9.5 g of potassium permanganate, while stirring at room temperature. The exothermic reaction, which starts immediately, can be controlled, if necessary, by external cooling with ice water. After 2 hours the mixture is filtered through diatomaceous earth, the acetone is stripped off from the filtrate under reduced pressure and the solution is filtered, if necessary with the aid of a filter aid, to give a clear filtrate. The filtrate is acidified with acetic acid and the fine precipitate which separates out is filtered off with suction and dissolved in 100 ml of N sodium hydroxide solution, the pH is brought back to 7.5 and the solution is again filtered to give a clear filtrate. The filtrate is acidified and 6-methyl-5-valeryl-benzimidazole-2-carboxylic acid, which precipitates immediately, is filtered off with suction, washed with water and dried in vacuo. The product starts to melt at 132°, with decomposition.

EXAMPLE 13

A solution of 30.1 g of 4-amino-3-nitro-bytyrophenone in 300 ml of methanol is treated with 3 g of Raney nickel and hydrogenated at 20°-35° under normal pressure. After 9.87 liters of hydrogen have been taken up, a solution of 21.9 g of glycollic acid in 50 ml of methanol is added under nitrogen, the catalyst is filtered off and the filtrate is evaporated to dryness. The evaporation residue is heated to 130° for 90 minutes and after cooling is dissolved in 600 ml of 2 N hydrochloric acid, the solution is filtered, the pH of the filtrate is adjusted to 8 and the resulting mixture is extracted with a total of about 2,000 ml of methylene chloride. The combined extracts are concentrated to about 200 ml under reduced pressure. The precipitate is filtered off, suspended in 200 ml of ethyl acetate, filtered off again and dried in vacuo. This gives 5(6)-butyryl-benzimidazole-2-methanol with a melting point of 141°-143°.

The starting material can be prepared as follows:

A solution of 18.3 g of 4-chloro-butyrophenone in 100 ml of sulphuric acid at −20° is treated, in the course of 5 minutes, at −20° to −15°, with a mixture of 40 ml of sulphuric acid and 21 ml of fuming nitric acid, whereupon everything dissolves. The solution is stirred for a further 45 minutes at −15° to −10° and poured onto 1,000 g of ice, the precipitate is filtered off, washed with water and taken up in chloroform, the chloroform solution is washed with a saturated solution of sodium bicarbonate and twice with water, dried over sodium sulphate and filtered and the filtrate is evaporated to dryness. The evaporation residue is digested with 25 ml of methanol. This gives 4-chloro-3-nitro-butyrophenone with a melting point of 52°-54°.

50 g of ammonia are injected into a solution of 22.8 g of 4-chloro-3-nitro-butyrophenone in 300 ml of ethanol in an autoclave. The mixture is warmed to 100° for 10 hours and after cooling to room temperature is evaporated to dryness under reduced pressure, the residue is warmed with 200 ml of 2 N hydrochloric acid to 80°-90° for 1 hour, the mixture is cooled to 15° by adding ice and filtered and the material on the filter is washed with water. The material on the suction filter is taken up in 1,000 ml of methylene chloride, the solution is dried over sodium sulphate, concentrated and treated with petroleum ether (boiling range 60°-80°) and all of the methylene chloride is evaporated. 4-Amino-3-nitro-butyrophenone, which has precipitated as crystals, is filtered off and dried in vacuo. It melts at 128°–129°.

EXAMPLE 14

A solution of 6.5 g of 5(6)-butyryl-benzimidazole-2-methanol in 300 ml of acetone and 60 ml of water is treated with 0.5 g of potassium permanganate and the mixture is cooled briefly in a water bath and stirred at room temperature for 3 hours. It is then filtered through diatomaceous earth, the acetone is stripped off under reduced pressure, the residue is extracted twice with chloroform, the chloroform solution is filtered through diatomaceous earth, if necessary using a filter aid, and the filtrate is acidified with 2 N acetic acid. 5(6)-Butyryl-benzimidazole-2-carboxylic acid, which has precipitated, is filtered off, washed with water and dried in vacuo. It melts at above 150°.

EXAMPLE 15

A solution of 35.5 g of 4-methylamino-3-nitro-acetophenone in 500 ml of methanol is treated with 4 g of Raney nickel and hydrogenated at 30°–35°. After 12.7 liters of hydrogen have been taken up, the mixture is treated, under nitrogen, with a solution of 27.3 g of glycollic acid in 100 ml of methanol, the catalyst is filtered off and the filtrate is evaporated to dryness under reduced pressure. The residue is heated to 130° for 90 minutes, under nitrogen. After cooling to room temperature, it is dissolved in 300 ml of 2 N hydrochloric acid and the solution is filtered, if necessary using a filter aid. The pH of the filtrate is brought to 7–8 with concentrated sodium hydroxide solution and finally with sodium carbonate solution and the mixture is extracted by shaking with methylene chloride. The methylene chloride phase is separated off and washed with water. The aqueous phase is extracted 5 times by shaking with methylene chloride. The combined methylene chloride phases are concentrated to 300 ml and the 5-acetyl-1-methyl-benzimidazole-2-methanol with a melting point of 178°–179°, which has precipitated, is filtered off. Further product with a melting point of 176°–177° can be obtained by concentrating the mother liquor to 100 ml.

The starting material can be prepared as follows:

A solution of 15.5 g of 4-chloroacetophenone in 100 ml of sulphuric acid at −20° is treated, in the course of 2 minutes, with a mixture of 40 ml of sulphuric acid and 21 ml of fuming nitric acid, the mixture is stirred for 1 hour at −25° to −20° and poured onto 600 g of ice and the precipitate is filtered off, washed with water and taken up in chloroform. The chloroform solution is washed with a saturated solution of sodium bicarbonate and twice with water, dried over sodium sulphate and filtered and the filtrate is evaporated to dryness. The evaporation residue is recrystallised from 50 ml of methanol. This gives 4-chloro-3-nitro-acetophenone with a melting point of 92°–95°.

39.9 g of 4-chloro-3-nitro-acetophenone are suspended in 200 ml of ethanol and the suspension is treated with 200 ml of a 33% strength aqueous solution of methylamine, stirred until crystallisation starts and then left to stand for several days, shaking occasionally. The mixture is evaporated to dryness under reduced pressure, 200 ml of 2 N hydrochloric acid are poured over the residue and the resulting mixture is warmed to 30°, allowed to cool, rendered alkaline and extracted with methylene chloride. The extract is washed with water, dried over sodium sulphate and filtered and the filtrate is evaporated. 4-Methylamino-3-nitro-acetophenone, which remains behind, is recrystallised from cyclohexane. It melts at 118°–120°.

EXAMPLE 16

In a manner analogous to that described in Example 12, 4.1 g of 5-acetyl-1-methyl-benzimidazole-2-methanol can be oxidised with 4 g of potassium permanganate to give 5-acetyl-1-methyl-benzimidazole-2-carboxylic acid with a melting point above 135°.

EXAMPLE 17

In a manner analogous to that described in Example 15, 5-butyryl-1-methyl-benzimidazole-2-methanol with a melting point of 153°–154° is obtained starting from 34.2 g of 4-chloro-3-nitro-butyrophenone, 100 ml of a 33% strength aqueous solution of methylamine and 20 g of glycollic acid, via 4-methylamino-3-nitro-butyrophenone with a melting point of 71°.

EXAMPLE 18

In a manner analogous to that described in Example 12, 18.5 g of 5-butyryl-1-methyl-benzimidazole-2-methanol can be oxidised with 18.5 g of potassium permanganate to give 5-butyryl-1-methyl-benzimidazole-2-carboxylic acid with a melting point above 90° (decomposition).

EXAMPLE 19

A solution of 18.8 g of 2-chloro-4-methylamino-5-nitro-butyrophenone in 190 ml of methanol is treated with 2 g of Raney nickel and hydrogenated at 20°–27° under normal pressure. After 5 liters of hydrogen have been taken up, a solution of 11.4 g of glycollic acid in 50 ml of methanol is added under nitrogen, the catalyst is filtered off and the filtrate is evaporated to dryness under reduced pressure. The residue is warmed to 130° for 1 hour, under nitrogen, and after cooling is ground with methanol, whereupon crystallisation starts. The crystalline product is cooled, filtered off and washed with cold methanol. This gives 5-butyryl-6-chloro-1-methyl-benzimidazole-2-methanol with a melting point of 183°–185°.

The starting material can be prepared as follows:

293 g of aluminium trichloride are added to 685 ml of m-dichlorobenzene, the mixture is warmed to 70° and 213 g of butyryl chloride are added dropwise, while stirring, at 70°–90° in the course of 30 minutes. The mixture is stirred for a further 2 hours at 80°–90° and after cooling is poured onto 3,000 g of ice and extracted with ethyl acetate. The extracts are washed successively with 2 N hydrochloric acid, water, 2 N sodium carbonate solution and twice with water, dried over sodium sulphate and highly concentrated, finally at 70° under a water pump vacuum. The residue is distilled. 2,4-Dichlorobutyrophenone has a boiling point at 12 mm Hg of 135°–141°.

A mixture of 24 ml of sulphuric acid and 7.5 ml of fuming nitric acid is added, in the course of 10 minutes, at −25° to −20°, to a solution, which has been cooled to −23°, of 32.6 g of 2,4-dichlorobutyrophenone in 130 ml of sulphuric acid and the resulting mixture is stirred for a further 15 minutes at −25° to −20°, poured onto ice and extracted with chloroform. The extracts are washed successively with water, sodium bicarbonate solution and twice with water, dried over sodium sulphate and evaporated. 2,4-Dichloro-5-nitro-butyrophenone with a melting point of 145°–50° can be further reacted as the crude product by dissolving 26.2 g of this product in 50 ml of ethanol and adding this solution dropwise to 150 ml of a 33% strength aqueous solution, which has been cooled to 8°, of methylamine. The mixture is stirred for a further 2 hours at 5° to 8° and evaporated to dryness under reduced pressure, the residue is treated with 150 ml of 2 N hydrochloric acid and the resulting mixture is warmed to 80°–90° for a few minutes. It is then cooled with ice to 10°, the precipitate is filtered off, washed with water and dissolved in methylene chloride, the resulting solution is dried over sodium sulphate, concentrated under reduced pressure, treated with cyclohexane and cooled to 15° and 2-chloro-4-methylamino-5-nitro-butyrophenone is filtered off. After drying it melts at 95°–97°.

EXAMPLE 20

In a manner analogous to that described in Example 12, 2.7 g of 5-butyryl-6-chloro-1-methyl-benzimidazole-2-methanol are oxidised with 2.5 g of potassium permanganate to give 5-butyryl-6-chloro-1-methyl-benzimidazole-2-carboxylic acid with a melting point of 90° (decomposition).

EXAMPLE 21

15.7 g of 2-methyl-4-methylamino-5-nitro-valerophenone in 180 ml of methanol are treated with 2 g of Raney nickel and hydrogenated under normal pressure and at 20°–35°. After 4.2 l of hydrogen have been taken up, a solution of 9.12 g of glycollic acid in 50 ml of methanol is added, under nitrogen, the catalyst is filtered off and the filtrate is evaporated to dryness. The residue is heated to 130° for 90 minutes, under nitrogen, and after cooling is dissolved in 100 ml of 2 N hydrochloric acid. The solution is filtered through diatomaceous earth, the filtrate is rendered alkaline and extracted with methylene chloride and the extract is washed twice with water, dried over sodium sulphate and evaporated. The residue is recrystallised from 100 ml of ethyl acetate. This gives 1,6-dimethyl-5-valeryl-benzimidazole-2-methanol with a melting point of 125°.

The starting material can be prepared as follows:

150 ml of a 33% strength aqueous solution of methylamine are poured over 17.5 g of crude mononitro-4-chloro-2-methyl-butyrophenone (containing about 50% of 4-chloro-2-methyl-5-nitro-butyrophenone) and, after leaving to stand for 4 hours at room temperature, the mixture is evaporated to dryness. The residue is dissolved in 100 ml of warm 2 N hydrochloric acid and the solution is rendered alkaline with sodium carbonate solution and extracted three times with methylene chloride. The extracts are washed twice with water, dried over sodium sulphate and evaporated. Crude 2-methyl-4-methylamino-5-nitro-valerophenone, which remains behind, is recrystallised from cyclohexane/petroleum ether and then melts at 72°–77°.

EXAMPLE 22

In a manner analogous to that described in Example 12, 4.7 g of 1,6-dimethyl-5-valeryl-benzimidazole-2-methanol are oxidised with 4.5 g of potassium permanganate to give 1,6-dimethyl-5-valeryl-benzimidazole-2-carboxylic acid with a melting point >88° (decomposition).

EXAMPLE 23

In a manner analogous to that described in Example 21, 1-ethyl-5-butyryl-6-methyl-benzimidazole-2-methanol with a melting point of 152°–154° can be prepared starting from crude mononitro-4-chloro-2-methyl-butyrophenone (containing about 75% of 4-chloro-2-methyl-5-nitro-butyrophenone) via 4-ethylamino-2-methyl-5-nitro-butyrophenone with a melting point of 118°–121°.

EXAMPLE 24

In a manner analogous to that described in Example 12, 5.2 g of 1-ethyl-5-butyryl-6-methyl-benzimidazole-2-methanol can be oxidised with 4.5 g of potassium permanganate to give 1-ethyl-5-butyryl-6-methyl-benzimidazole-2-carboxylic acid with a melting point >80° (decomposition).

EXAMPLE 25

In a manner analogous to that described in Example 15, 5-acetyl-1-n-butyl-benzimidazole-2-methanol with a melting point of 121°–124° can be prepared starting from 4-chloro-3-nitro-acetophenone via 4-butylamino-3-nitro-acetophenone with a melting point of 69°–71°.

EXAMPLE 26

In a manner analogous to that described in Example 12, 4.9 g of 5-acetyl-1-n-butyl-benzimidazole-2-methanol can be oxidised with 4.5 g of potassium permanganate to give 5-acetyl-1-n-butyl-benzimidazole-2-carboxylic acid with a melting point >75° (decomposition).

EXAMPLE 27

In a manner analogous to that described in Example 21, 1-n-butyl-5-butyryl-6-methyl-benzimidazole-2-methanol with a melting point of 78°–81° is obtained starting from crude mono-nitro-4-chloro-2-methyl-butyrophenone (containing about 50% of 4-chloro-2-methyl-5-nitro-butyrophenone) via 4-butylamino-2-methyl-5-nitro-butyrophenone with a melting point of 80°–82°.

EXAMPLE 28

In a manner analogous to that described in Example 12, 4.4 g of 1-n-butyl-5-butyryl-6-methyl-benzimidazole-2-methanol can be oxidised to 1-n-butyl-5-butyryl-6-methyl-benzimidazole-2-carboxylic acid with a melting point >70° (decomposition).

EXAMPLE 29

2.5 g of 5-butyryl-6-methyl-benzimidazole-2-carboxylic acid are dissolved in 100 ml of 0.1 N sodium hydroxide solution and the solution is treated with 14.5 g of sodium carbonate. 38 g of triethyloxonium tetrafluoborate are added in portions, in the course of 10 minutes, to the resulting suspension. The mixture is stirred for a further 30 minutes and extracted with ethyl acetate and the extract is washed twice with water, dried over sodium sulphate and evaporated to dryness. The evaporation residue is chromatographed on 100 g of silica gel using chloroform as the eluant. This gives ethyl 5-butyryl-6-methyl-benzimidazole-2-carboxylate with a melting point of 142°–144°.

EXAMPLE 30

A mixture of 2.5 g of 5-butyryl-6-methyl-benzimidazole-2-carboxylic acid, 1.91 g of dimethylformamide diethyl acetal and 25 ml of acetonitrile is left to stand for 2 days at room temperature, with the exclusion of moisture and with occasional shaking. The acetonitrile is stripped off under reduced pressure, the residue is partitioned between ethyl acetate and sodium bicarbonate solution, the neutral phase is washed with water and evaporated and the residue is chromatographed on aluminium oxide using chloroform/ethanol (9:1) and ethyl 5-butyryl-6-methyl-benzimidazole-2-carboxylate with a melting point of 142°–144° is obtained.

EXAMPLE 31

19.1 g of 5-butyryl-6-methyl-benzimidazole-2-carboxylic acid are added, in the course of 5 minutes, to a mixture of 62.9 g of diethyl pyrocarbonate, 100 ml of triethylamine and 500 ml of acetonitrile, while stirring. The mixture is stirred further, first for 1 hour at room temperature and then for 6 hours at the boil, and evaporated to dryness under reduced pressure, the residue is taken up in ethyl acetate, the solution is washed with sodium bicarbonate solution and twice with water, dried over sodium sulphate and evaporated and the residue is recrystallised from ethyl acetate/methylene chloride. This gives ethyl 5-butyryl-6-methyl-benzimidazole-2-carboxylate with a melting point of 146°–147°.

EXAMPLE 32

22.2 g of 4-amino-2-methyl-5-nitro-butyrophenone are dissolved in 230 ml of methanol, treated with 2 g of Raney nickel and hydrogenated at 15°–25° under normal pressure until 4.9 liters of hydrogen have been taken up. 20.8 g of ethoxyacetic acid are added, under nitrogen, the catalyst is filtered off, the filtrate is evaporated under reduced pressure and the residue is heated at 130° for 3 hours. After cooling, it is dissolved in 200 ml of 2 N hydrochloric acid, the solution is washed twice with ethyl acetate, rendered alkaline in the cold with sodium carbonate and extracted twice with ethyl acetate, the extracts are dried over sodium sulphate and evaporated and the residue is chromatographed on 300 g of silica gel. An initial fraction is first eluted with 1,200 ml of chloroform and 2-ethoxymethyl-5-butyryl-6-methyl-benzimidazole is then eluted with 1,200 ml of chloroform/ethanol (24:1).

EXAMPLE 33

15 g of potassium permanganate are added to a solution, which has been cooled to 10°, of 18.9 g of 2-ethoxymethyl-5-butyryl-6-methyl-benzimidazole in 380 ml of acetone, 9.5 ml of pyridine and 5.7 ml of water, while stirring. The mixture is stirred for 1 hour while cooling with ice and for 40 hours at room temperature and filtered, the filtrate is evaporated to dryness under reduced pressure, the residue is taken up in ethyl acetate and the resulting solution is washed successively with sodium bicarbonate solution, which has been buffered to pH 6, and twice with water, dried over sodium sulphate and evaporated under reduced pressure. The residue is then taken up in 30 ml of warm ethyl acetate, the solution is left to stand overnight and crystalline ethyl 5-butyryl-6-methyl-benzimidazole-2-carboxylate with a melting point of 137°–139° is filtered off. Further product with a melting point of 129°–132° can be obtained from the mother liquor. Recrystallisation from ethyl acetate/methylene chloride raises the melting point to 146°–147°.

EXAMPLE 34

6.0 g of 5-butyryl-1,6-dimethyl-benzimidazole-2-carboxylic acid are introduced, in the course of 15 minutes, into a mixture of 150 ml of acetonitrile, 15 ml of triethylamine and 18.5 g of diethyl pyrocarbonate, while stirring at room temperature. The mixture is left to stand overnight, the acetonitrile is stripped off under reduced pressure, the residue is taken up in ethyl acetate and the resulting solution is washed with water, dried over sodium sulphate and evaporated to dryness. Ethyl 5-butyryl-1,6-dimethyl-benzimidazole-2-carboxylate, which is initially obtained as an oil but soon crystallises, is filtered off. When recrystallised from ethyl acetate/cyclohexane, it melts at 106°–108°.

EXAMPLE 35

In a manner analogous to that described in Example 31, ethyl 5-butyryl-1-methyl-benzimidazole-2-carboxylate with a melting point of 115°–117° is obtained starting from 10.1 g of 5-butyryl-1-methyl-benzimidazole-2-carboxylic acid and 20 g of diethyl pyrocarbonate.

EXAMPLE 36

In a manner analogous to that described in Example 32, 2-ethoxymethyl-5-butyryl-1,6-dimethyl-benzimidazole with a melting point of 46°–47° is obtained starting from 23.6 g of 2-methyl-4-methylamino-5-nitro-butyrophenone and 10.4 g of ethoxyacetic acid.

EXAMPLE 37

16.5 ml of half-concentrated hydrochloric acid are poured over 23.4 g of 3,4-diamino-benzophenone and 12.7 g of glycollic acid and the mixture is heated at 130°–140° for 105 minutes. It is poured, while still hot, into 1,500 ml of ice water, the resulting mixture is rendered alkaline with concentrated ammonia solution and stirred for 60 minutes at room temperature and the precipitate is filtered off with suction. The material on the suction filter is boiled with ethyl acetate, the mixture is cooled and the product is again filtered off with suction. This gives 5(6)-benzoyl-benzimidazole-2-methanol with a melting point of 226°–227°.

The starting material can be obtained starting from 20.8 g of 4-chloro-3-nitro-benzophenone by warming for 15 hours with 20 g of ammonia, dissolved in 290 g of methanol and 52 g of sulpholane, to 125° in a bomb tube and hydrogenating the 4-amino-3-nitro-benzophenone, which is thus obtainable, under normal pressure in methanol and in the presence of Raney nickel. The product melts at 80°–83°.

EXAMPLE 38

4 g of 5(6)-benzoyl-benzimidazole-2-methanol are dissolved in 180 ml of acetone and 55 ml of water with gentle warming and oxidised with 2.8 g of potassium permanganate, dissolved in 40 ml of water, in a manner analogous to that described in Example 10, to give 5(6)-benzoyl-benzimidazole-2-carboxylic acid. 5-Benzoyl-1-methyl-benzimidazole-2-carboxylic acid can also be prepared in an analogous manner.

EXAMPLE 39

In a manner analogous to that described in Example 37, 5-benzoyl-1-methyl-benzimidazole-2-methanol with a melting point of 168°–172° is obtained starting from 13.2 g of 3-amino-4-methylamino-benzophenone, 6.6 g of glycollic acid and 9.24 ml of half-concentrated hydrochloric acid. This product can be further purified on 30 times the amount of silica gel using ethyl acetate-/acetone (7:3) as the eluant and then melts at 176°.

The starting material can be prepared as follows:

11 g of 4-chloro-3-nitro-benzophenone, 20 g of methylamine, 153.4 g of methanol and 27.5 g of sulpholane are warmed to 125° for 15 hours in a closed vessel. The reaction solution is evaporated to dryness, the residue is boiled thoroughly with 400 ml of 2 N hydrochloric acid for 20 minutes and the precipitate is filtered off, washed with water and dissolved in methylene chloride. After drying over sodium sulphate and evaporating, 4-methylamino-3-nitro-benzophenone with a melting point of 198°–201° is obtained.

15.5 g of 4-methylamino-3-nitro-benzophenone in 350 ml of methanol are treated with 3 g of Raney nickel and hydrogenated at 20°–25° under normal pressure. After 3.8 liters of hydrogen have been taken up, the catalyst is filtered off and the filtrate is evaporated to dryness under reduced pressure. 3-Amino-4-methylamino-benzophenone crystallises on grinding and after filtering off with suction and drying this melts at 127°–130°.

EXAMPLE 40

22 g of 2-methoxy-4-methylamino-5-nitro-butyrophenone are dissolved in 250 ml of methanol, treated with 2 g of Raney nickel and hydrogenated at 35°–40° under normal pressure. After 5.9 liters of hydrogen have been taken up, a solution of 12.9 g of glycollic acid in 20 ml of methanol is added, under nitrogen, the catalyst is filtered off, the filtrate is evaporated to dryness and the residue is heated at 150° for 1 hour. It is allowed to cool and dissolved in 100 ml of 2 N hydrochloric acid, the solution is filtered, the filtrate is rendered alkaline with sodium hydroxide solution and extracted with 2,000 ml of methylene chloride, the extract is highly concentrated under reduced pressure and treated with ethyl acetate, all of the methylene chloride is stripped off, the residual mixture is cooled and the precipitate is filtered off and washed with ethyl acetate/petroleum ether. 5-Butyryl-6-methoxy-1-methyl-benzimidazole-2-methanol melts at 179°–184°.

The starting material can be prepared as follows:

Sodium methylate freshly prepared from 0.23 g of sodium and 25 ml of methanol is suspended, while still moist, in 10 ml of hexamethylphosphoric acid triamide, under nitrogen, and the suspension is treated with 2.45 g of 2-chloro-4-methylamino-5-nitro-butyrophenone. An exothermic reaction starts. The mixture is stirred for a further 2 hours at room temperature, treated with water and extracted with ethyl acetate. The extract is washed with water, dried over sodium sulphate and evaporated and the residue is recrystallised from ethyl acetate. 2-Methoxy-4-methylamino-5-nitro-butyrophenone melts at 165°–166°.

EXAMPLE 41

In a manner analogous to that described in Example 12, 5.2 g of 5-butyryl-6-methoxy-1-methyl-benzimidazole-2-methanol are oxidised with 4.5 g of potassium permanganate to give 5-butyryl-6-methoxy-1-methyl-benzimidazole-2-carboxylic acid with a melting point above 85° (decomposition)

EXAMPLE 42

A solution of 15.0 g of crude 5-amino-2-methyl-4-methylamino-cyclopropylcarbonylbenzene in 200 ml of absolute methanol is treated with 6.25 g of glycollic acid. The mixture is then stirred at 35° for 15 minutes, under a nitrogen atmosphere, and evaporated to dryness under reduced pressure. The crystalline residue is heated to 130° and stirred at this temperature for three hours. The melt is cooled and dissolved in 300 ml of 2 N hydrochloric acid. The acid solution is rendered alkaline with 2 N sodium bicarbonate solution. The oil which has separated out is extracted with methylene chloride and the organic extract is washed with water, dried over magnesium sulphate and concentrated to dryness under reduced pressure. The residue is chromatographed on 400 g of silica gel using methylene chloride/methanol (9:1) as the eluant. 700 ml fractions are collected. 5-Cyclopropylcarbonyl-1,6-dimethylbenzimidazole-2-methanol is contained in fractions 3–8 and these are combined and evaporated under reduced pressure. When crystallised from ethyl acetate, the compound melts at 143°–144°.

The starting material can be prepared as follows:

A suspension of 428 g of 3-chloro-toluene and 174.6 g of powdered aluminium chloride is treated with 124 g of cyclopropanecarboxylic acid chloride in the course of one hour. The reaction mixture is then heated to 50° for one hour and poured onto 1,000 g of ice. The oil which has separated out is extracted with 1,000 ml of ether. The organic phase, which has been separated off, is washed with twice 200 ml of 2 N hydrochloric acid, 200 ml of 2 N sodium carbonate solution and water, dried over magnesium sulphate and concentrated to dryness. The residue, which is thus obtained, is distilled. This gives a mixture of 4-chloro-2-methylcyclopropylcarbonyl-benzene and the isomeric 2-chloro-4-methylcyclopropylcarbonyl-benzene in a ratio of 2:1. Boiling point 100°–102°/0.05 mm Hg.

123 g of a mixture of isomers comprising 4-chloro-2-methyl-cyclopropylcarbonyl-benzene and 2-chloro-4-methyl-cyclopropylcarbonyl-benzene are added dropwise to 538 ml of concentrated sulphuric acid, which has been cooled to $-20°$ to $-25°$, while stirring well. The solution is treated, at $-20°$ to $-25°$, in the course of 30 minutes with a mixture of 31.3 ml of 100% strength nitric acid (d: 1.52) and 101.2 ml of concentrated sulphuric acid and the mixture is then stirred for a further 10 minutes, during which time the temperature rises to $-10°$. The mixture is poured into 6,000 ml of water and the oil which has separated out is extracted with 2,000 ml of ether. The organic phase is washed twice with water, then twice with, in each case, 300 ml of 2 N potassium bicarbonate solution and again with water, dried over magnesium sulphate and evaporated. The residue, which is an oil, consits of a mixture, about 2/3 of which comprises 4-chloro-2-methyl-5-nitro-cyclopropylcarbonyl-benzene and which additionally contains an isomer, probably 2-chloro-4-methyl-5-cyclopropyl-carbonyl-benzene, and this mixture is further reacted without further purification.

127 g of this mixture of isomers which contains 4-chloro-2-methyl-5-nitro-cyclopropylcarbonyl-benzene in addition to 2-chloro-4-methyl-5-nitro-cyclopropyl-carbonyl-benzene are treated with 600 ml of a 33% strength solution of methylamine in ethanol. The oily starting material dissolves and a yellow coloration develops. The mixture is left to stand for 30 minutes at room temperature and is then concentrated to dryness under reduced pressure. The residue is treated with 2,000 ml of methylene chloride, ice and sodium carbonate, the mixture is shaken and the organic phase is separated off. This is washed with water, dried over magnesium sulphate and evaporated to dryness under reduced pressure. The residue is crystallised from ethyl acetate. 2-Methyl-4-methylamino-5-nitro-cyclopropylcarbonyl-benzene melts at 144°–148°.

After adding 2.8 g of Raney nickel, a solution of 5-nitro-2-methyl-4-methylamino-cyclopropylcarbonyl-benzene in 280 ml of methanol is hydrogenated for 8 hours at 25° and under normal pressure. After the hydrogenation has ended, the catalyst is filtered off under a nitrogen atmosphere and the methanolic solution of unstable 5-amino-2-methyl-4-methylamino-cyclopropylcarbonyl-benzene is immediately reacted further.

EXAMPLE 43

A solution of 1.6 g of 5-cyclopropyl-carbonyl-6-methyl-benzimidazole-2-methanol in 93 ml of acetone is diluted with 72 ml of water, while stirring. This solution is treated with 1.6 g of potassium permanganate and stirred at room temperature for 15 hours. The suspension is then concentrated under reduced pressure to about 70 ml and filtered through a layer of diatomaceous earth. The material on the filter is then washed with 40 ml of water and the aqueous filtrate is acidified with 2 N hydrochloric acid. The precipitate formed is filtered off, washed with 10 ml of water, suspended in 10 ml of cold methanol and filtered off again. 5-Cyclopropylcarbonyl-6-methyl-benzimidazole-2-carboxylic acid melts at 89°–92° (decomposition).

EXAMPLE 44

A solution of 5.0 g of 5-butyryl-1,6-dimethyl-benzimidazole-2-methanol in 100 ml of methylene chloride is treated with 2.36 g of acetyl chloride, stirred for one hour at room temperature and then treated with 5 ml of triethylamine. The mixture is stirred for a further 30 minutes and extracted by shaking with sodium bicarbonate solution and twice with water and the extracts are dried over sodium sulphate and evaporated. This gives 2-acetoxymethyl-5-butyryl-1,6-dimethyl-benzimidazole with a melting point of 95.5°–96°.

EXAMPLE 45

27.8 g of 2-methyl-4-methylamino-5-nitro-oenanthophenone, dissolved in 300 ml of methanol, are treated with 9 g of Raney nickel and hydrogenated at 20° to 25° under normal pressure until 6.8 liters of hydrogen have been taken up. The hydrogenation solution is treated, under nitrogen, with a solution of 15 g of glycollic acid in 50 ml of methanol, the catalyst is filtered off and the filtrate is evaporated under reduced pressure. The evaporation residue is heated at 130° for 90 minutes, under nitrogen, and after cooling is dissolved in 2 N hydrochloric acid, the solution is filtered and the filtrate is rendered alkaline with concentrated sodium hydroxide solution and extracted with methylene chloride. The organic phases are collected, washed twice with water, dried over sodium sulphate and evaporated. This gives 1,6-dimethyl-5-oenanthylbenzimidazole-2-methanol with a melting point of 93°–93.5°.

The starting material can be prepared as follows:

60.6 g of 4-chloro-2-methyl-benzonitrile, dissolved in 60 ml of diethyl ether, are added dropwise to a boiling solution of n-hexyl-magnesium bromide, prepared from 12.1 g of magnesium turnings and 82.5 g of 1-bromohexane in 125 ml of diethyl ether. The reaction mixture is heated to the boil for 5 hours. After cooling, 150 ml of 4 N hydrochloric acid are added dropwise. The mixture is stirred for a further 60 minutes and left to stand overnight, the ether phase is separated off, the aqueous phase is washed with ether, the combined ether phases are washed with water, dried over sodium sulphate and evaporated and the residue is distilled. 4-Chloro-2-methyl-oenanthophenone passes over at a boiling point/10 mm Hg of 165°–170°.

67.7 g of 4-chloro-2-methyl-oenanthophenone are dissolved in 285 ml of sulphuric acid, which has been cooled to −15° to −10°, and the solution is treated dropwise, in the course of 15 minutes, with a mixture of 16.3 ml of fuming nitric acid and 53 ml of sulphuric acid. The mixture is stirred for a further 30 minutes at −15°, poured into 1,500 ml of ice water and extracted with methylene chloride. The organic phase is washed successively with water, sodium bicarbonate solution and twice with water, dried over sodium sulphate and evaporated. 4-Chloro-2-methyl-5-nitro-oenanthophenone can be reacted further without further purification.

78.8 g of 4-chloro-2-methyl-5-nitro-oenanthophenone are dissolved in 600 ml of ethanol and the solution is treated with 200 ml of a 33% strength aqueous solution of methylamine, heated on a water bath for 60 minutes and left to stand overnight at room temperature. The mixture is evaporated to dryness and the residue is heated with 300 ml of 2 N hydrochloric acid to 80° to 90° for 60 minutes and the mixture is cooled to 10° to 15° by adding ice, the precipitate is filtered off and taken up in methylene chloride, the solution is dried over sodium sulphate and again evaporated to dryness, the residue is ground with 200 ml of petroleum ether (60°–80°) and 2-methyl-4-methylamino-5-nitro-oenanthophenone with a melting point of 77°–79° is filtered off.

EXAMPLE 46

11.6 g of ethyl 5-(1-hydroxybutyl)-1,6-dimethyl-2-ethoxy-methylbenzimidazole-2-carboxylate are dissolved in 400 ml of acetone and 100 ml of water and the solution is cooled to +5° and treated with 10 g of potassium permanganate. The mixture is stirred for 2 hours at +5° and overnight at room temperature, the manganese dioxide is filtered off, the acetone is stripped from the filtrate under reduced pressure, the residue is exhaustively extracted with ethyl acetate and the extract is dried over sodium sulphate, highly concentrated under reduced pressure and ground with cyclohexane. This gives ethyl 5-butyryl-1,6-dimethyl-benzimidazole-2-carboxylate with a melting point of 106°–108°.

The starting material can be obtained, for example, by hydrogenating 2-methyl-4-methylamino-5-nitro-butyrophenone in the presence of palladium on charcoal at atmospheric pressure and 25° to 50° and condensing 3-(1-hydroxybutyl)-4-methyl-2-methylamino-aniline which can be thus obtained, with ethoxyacetic acid in the presence of diluted hydrochloric acid treating the reaction product, if necessary, with aqueous potassium acetate solution in order to hydrolyse any 5-(1-chlorobutyl-1,6-dimethyl-2-ethoxymethyl-benzimidazole which may have been formed. The 5-(1-hydroxybutyl)-1,6-dimethyl-2-ethoxymethylbenzimidazole can be used without further purification.

EXAMPLE 47

5-Butyryl-6-hydroxy-1-methyl-benzimidazole-2-carboxylic acid, 5-butyryl-6-hydroxy-1-methyl-benzimidazole-2-methanol, 1,6-dimethyl-5-(4-methylthiobutyryl)-benzimidazole-2-methanol 5-isobutyryl-1,6-dimethyl-benzimidazole-2-methanol, m.p. 148°–150°, 5-isobutyryl-1,6-dimethyl-benzimidazole-2-carboxylic acid m.p. 158°–160°, 5-propionyl-1,6-dimethyl-benzimidazole-2-methanol, m.p. 139°–140° C., 5-(2-methylbutyryl)-1,6-dimethyl-benzimidazole-2-methanol, m.p. 158°, 5-isovaleryl-1,6-dimethyl-benzimidazole-2-methanol, m.p. 142°–142.5°, 5-butyryl-1,6-dimethyl-benzimidazole-2-carboxylic acid isopropyl ester, m.p. 90°–91°, 5-butyryl-1,6-dimethyl-benzimidazole-2-carboxylic acid (1-dimethylamino)-2-propyl ester, 5-propionyl-1,6-dimethyl-benzimidazole-2-carboxylic acid ester and 5-butyryl-1,6-dimethyl-2-(2-dimethylaminoethoxymethyl)-benzimidazole can also be prepared in a manner analogous to that described in Examples 10–45.

EXAMPLE 48

A 2% strength aqueous solution, which is suitable for inhalation, of the sodium salt of 5-butyryl-6-methyl-benzimidazole-2-carboxylic acid can be prepared as follows:

| Composition (for 100 ml) | |
|---|---|
| Sodium salt of 5-butyryl-6-methyl-benzimidazole-2-carboxylic acid | 2.000 g |
| Disodium salt of ethylenediaminetetraacetic acid (stabiliser) | 0.010 g |
| Benzalkonium chloride (preservative) | 0.010 g |
| Distilled water | ad 100 ml |

The sodium salt of 5-butyryl-6-methyl-benzimidazole-2-carboxylic acid is dissolved in freshly distilled water and the solution is treated with the disodium salt of ethylenediaminetetraacetic acid and the benzalkonium chloride (mixture of alkyl-dimethyl-benzyl-ammonium chlorides in which alkyl contains from 8 to 18 carbon atoms). After the components have completely dissolved, the resulting solution is made up to a volume of 100 ml with water, filled into a container and sealed gas-tight.

EXAMPLE 49

A 2% strength aqueous solution, which is suitable for inhalation, of the sodium salt of 5-butyryl-1,6-dimethyl-benzimidazole-2-carboxylic acid can be prepared as follows:

| Composition (for 100 ml) | |
|---|---|
| Sodium salt of 5-butyryl-1,6-dimethyl-benzimidazole-2-carboxylic acid | 2.000 g |
| Disodium salt of ethylenediaminetetraacetic acid (stabiliser) | 0.010 g |
| Benzalkonium chloride (preservative) | 0.010 g |
| Distilled water | ad 100 ml |

The sodium salt of 5-butyryl-1,6-dimethyl-benzimidazole-2-carboxylic acid is dissolved in freshly distilled water and the solution is treated with the disodium salt of ethylenediaminetetraacetic acid and the benzalkonium chloride (mixture of alkyl-dimethyl-benzyl-ammonium chlorides in which alkyl contains from 8 to 18 carbon atoms). After the components have completely dissolved, the resulting solution is made up to a volume of 100 ml with water, filled into a container and sealed gas-tight.

2% strength aqueous inhalation solutions of the sodium salt of 5(6)-valeryl-benzimidazole-2-carboxylic acid, 5-acetyl-6-methyl-benzimidazole-2-carboxylic acid, 6-methyl-5-propionyl-benzimidazole-2-carboxylic acid, 6-methyl-5-valeryl-benzimidazole-2-carboxylic acid, 5(6)-butyryl-benzimidazole-2-carboxylic acid, 5-butyryl-6-methoxy-benzimidazole-2-carboxylic acid, 5-butyryl-6-chloro-benzimidazole-2-carboxylic acid, 5-cyclopropylcarbonyl-6-methyl-2-benzimidazole-2-carboxylic acid, 5-cyclohexylcarbonyl-6-methyl-2-benzimidazole-2-carboxylic acid, 5-(4-methoxybutyryl)-6-methyl-2-benzimidazole-2-carboxylic acid, 6-methyl-5-(4-methylthiobutyryl)-benzimidazole-2-carboxylic acid, 6-methyl-5-(4-methylsulphinylbutyryl)-benzimidazole-2-carboxylic acid, 6-methyl-5-(4-phenylthiobutyryl)-benzimidazole-2-carboxylic acid, 6-methyl-5-(4-phenylsulphinylbutyryl)-benzimidazole-2-carboxylic acid, 5-acetyl-1-methyl-benzimidazole-2-carboxylic acid, 5-butyryl-1-methyl-benzimidazole-2-carboxylic acid, 5-butyryl-6-chloro-1-methyl-benzimidazole-2-carboxylic acid, 1,6-dimethyl-5-valeryl-benzimidazole-2-carboxylic acid, 1-ethyl-5-butyryl-6-methyl-benzimidazole-2-carboxylic acid, 5-acetyl-1-butyl-benzimidazole-2-carboxylic acid, 1-butyl-5-butyryl-benzimidazole-2-carboxylic acid, 5(6)-benzoyl-benzimidazole-2-carboxylic acid, 5-cyclopropylcarbonyl-1,6-dimethyl-benzimidazole-2-carboxylic acid and 5-butyryl-6-hydroxy-1-methyl-benzimidazole-2-carboxylic acid can be prepared in an analogous manner.

EXAMPLE 50

A 2% strength aqueous solution, which is suitable for inhalation, of 5-butyryl-1,6-dimethyl-benzimidazole-2-methanol can be prepared as follows:

| Composition (for 100 ml) | |
|---|---|
| 5-Butyryl-6-methyl-benzimidazole-2-methanol | 2.000 g |
| Disodium salt of ethylenediaminetetraacetic acid (stabiliser) | 0.010 g |
| Benzalkonium chloride (preservative | 0.010 g |
| Distilled water | ad 100 ml |

The 5-butyryl-1,6-dimethyl-benzimidazole-2-methanol is dissolved in freshly distilled water with the addition of the solubilising agent, for example polyethylene glycol, and the solution is treated with the disodium salt of ethylenediaminetetraacetic acid and the benzalkonium chloride (mixture of alkyl-dimethyl-benzyl-ammonium chlorides in which alkyl contains from 8 to 18 carbon atoms). After the components have completely dissolved, the resulting solution is made up to a volume of 100 ml with water, filled into a container and sealed gas-tight.

2% strength aqueous inhalation solutions of 5-butyryl-6-methyl-benzimidazole-2-methanol, 5(6)-valeryl-benzimidazole-2-methanol, 6-methyl-5-valeryl-benzimidazole-2-methanol, 5(6)-butyryl-benzimidazole-2-methanol, 5-acetyl-1-methyl-benzimidazole-2-methanol, 5-butyryl-1-methyl-benzimidazole-2-methanol, 5-butyryl-6-chloro-1-methyl-benzimidazole-2-methanol, 1,6-dimethyl-5-valeryl-benzimidazole-2-methanol, 1-ethyl-5-butyryl-6-methyl-benzimidazole-2-methanol, 5-acetyl-1-butyl-benzimidazole-2-methanol, 1-butyl-5-butyryl-6-methyl-benzimidazole-2-methanol, 5-benzoyl-benzimidazole-2-methanol, 5-benzoyl-benzimidazole-2-methanol, 5-butyryl-6-methoxy-1-methylbenzimidazole-2-methanol, 1,6-dimethyl-5-oenanthyl-benzimidazole-2-methanol, 5-cyclopropylcarbonyl-1,6-dimethyl-benzimidazole-2-methanol, 2-ethoxymethyl-5-butyryl-6-methyl-benzimidazole, 2-ethoxymethyl-5-butyryl-1,6-dimethyl-benzimidazole, 2-acetoxymethyl-5-butyryl-1,6-dimethyl-benzimidazole, 5-butyryl-6-hydroxy-1-methyl-benzimidazole-2-methanol, 1,6-dimethyl-5-(4-methylthiobutyryl)-benzimidazole-2-methanol, 5-butyryl-1,6-dimethyl-2-(2-dimethylaminoethoxy-methyl)-benzimidazole, ethyl 5-butyryl-6-methyl-benzimidazole-2-carboxylate, ethyl 5-butyryl-1,6-dimethyl-benzimidazole-2-carboxylate, ethyl 5-butyryl-1-methyl-benzimidazole-2-carboxylate and methyl 5-butyryl-6-methyl-benzimidazole-2-carboxylate can be prepared in an analogous manner.

EXAMPLE 51

Capsules containing 0.025 g of 5-butyryl-6-methyl-benzimidazole-2-carboxylic acid, which are suitable for insufflation, can be prepared as follows:

| Composition (for 1,000 capsules) | |
|---|---|
| 5-Butyryl-6-methyl-benzimidazole-2-carboxylic acid | 25.00 g |
| Ground lactose | 25.00 g |

The 5-butyryl-6-methyl-benzimidazole-2-carboxylic acid and the lactose (very finely ground) are mixed together well. The resulting powder is then sieved and 0.05 g portions are filled into gelatine capsules.

EXAMPLE 52

Capsules containing 0.025 g of 5-butyryl-1,6-dimethyl-benzimidazole-2-carboxylic acid, which are suitable for insufflation, can be prepared as follows:

| Composition (for 1,000 capsules) | |
|---|---|
| 5-Butyryl-1,6-dimethyl-benzimidazole-2-carboxylic acid | 25.00 g |
| Ground lactose | 25.00 g |

The 5-butyryl-1,6-dimethyl-benzimidazole-2-carboxylic acid and the lactose (very finely ground) are mixed together well. The resulting powder is then sieved and 0.05 g portions are filled into gelatine capsules.

Insufflation capsules containing, in each case, 0.025 g of 5(6)-valeryl-benzimidazole-2-carboxylic acid, 5-acetyl-6-methyl-benzimidazole-2-carboxylic acid, 6-methyl-5-propionyl-benzimidazole-2-carboxylic acid, 6-methyl-5-valeryl-benzimidazole-2-carboxylic acid, 5(6)-butyryl-benzimidazole-2-carboxylic acid, 5-butyryl-6-methoxy-benzimidazole-2-carboxylic acid, 5-butyryl-6-chloro-benzimidazole-2-carboxylic acid, 5-cyclopropyl-carbonyl-6-methyl-benzimidazole-2-carboxylic acid, 5-cyclohexylcarbonyl-6-methyl-benzimidazole-2-carboxylic acid, 5-(4-methoxybutyryl)-6-methyl-benzimidazole-2-carboxylic acid, 6-methyl-5-(4-methylthiobutyryl)-benzimidazole-2-carboxylic acid, 6-methyl-5-(4-methylsulphinylbutyryl)-benzimidazole-2-carboxylic acid, 6-methyl-5-(4-phenylthiobutyryl)-benzimidazole-2-carboxylic acid, 6-methyl-5-(4-phenylsulphinyl-butyryl)-benzimidazole-2-carboxylic acid, methyl 5-butyryl-6-methyl-benzimidazole-2-carboxylate, 5-butyryl-6-methyl-benzimidazole-2-methanol, 5-butyryl-1,6-dimethyl-benzimidazole-2-methanol, 5(6)-valeryl-benzimidazole-2-methanol, 6-methyl-5-valeryl-benzimidazole-2-methanol, 5(6)-butyryl-benzimidazole-2-methanol, 5-acetyl-1-methyl-benzimidazole-2-methanol, 5-butyryl-1-methyl-benzimidazole-2-methanol, 5-butyryl-6-chloro-1-methyl-benzimidazole-2-methanol, 1,6-dimethyl-5-valeryl-benzimidazole-2-methanol, 1-ethyl-5-butyryl-6-methyl-benzimidazole-2-methanol, 5-acetyl-1-butyl-benzimidazole-2-methanol, 1-butyl-5-butyryl-6-methyl-benzimidazole-2-methanol, 5-benzoyl-benzimidazole-2-methanol, 5-benzoyl-1-methyl-benzimidazole-2-methanol, 5-butyryl-6-methoxy-1-methyl-benzimidazole-2-methanol, 5-cyclopropylcarbonyl-1,6-dimethyl-benzimidazole-2-methanol, 2-ethoxymethyl-5-butyryl-6-methyl-benzimidazole, 2-ethoxymethyl-5-butyryl-1,6-dimethyl-benzimidazole, 2-acetoxymethyl-5-butyryl-1,6-dimethyl-benzimidazole, 5-butyryl-6-hydroxy-1-methyl-benzimidazole-2-methanol, 1,6-dimethyl-5-(4-methylthiobutyryl)-benzimidazole-2-methanol, 5-butyryl-1,6-dimethyl-2-(2-dimethylaminoethoxymethyl)-benzimidazole, 5-acetyl-1-methyl-benzimidazole-2-carboxylic acid, 5-butyryl-1-methyl-benzimidazole-2-carboxylic acid, 5-butyryl-6-chloro-1-methyl-benzimidazole-2-carboxylic acid, 1,6-dimethyl-5-valeryl-benzimidazole-2-carboxylic acid, 1-ethyl-5-butyryl-6-methyl-benzimidazole-2-carboxylic acid, 5-acetyl-1-butyl-benzimidazole-2-carboxylic acid, 1,6-dimethyl-5-oenanthyl-benzimidazole-2-methanol, 1-butyl-5-butyryl-benzimidazole-2-carboxylic acid, 5(6)-benzoyl-benzimidazole-2-carboxylic acid, 5-cyclopropylcarbonyl-1,6-dimethyl-benzimidazole-2-carboxylic acid, 5-butyryl-6-hydroxy-1-methyl-benzimidazole-2-carboxylic acid, ethyl 5-butyryl-6-methyl-benzimidazole-2-carboxylate, ethyl 5-butyryl-1,6-dimethyl-benzimidazole-2-carboxylate or ethyl 5-butyryl-1-methyl-benzimidazole-2-carboxylate can also be prepared in an analogous manner.

EXAMPLE 53

Tablets containing 100 mg of butyryl-1,6-dimethyl-benzimidazole-2-carboxylic acid or its sodium salt (active compound) can be prepared, for example, in the following composition:

| Composition | Per Tablet |
|---|---|
| Active compound, for example 5-butyryl-1,6-dimethyl-benzimidazole-2-carboxylic acid | 100 mg |
| Lactose | 50 mg |
| Wheat starch | 73 mg |
| Colloidal silica | 13 mg |
| Talc | 12 mg |
| Magnesium stearate | 2 mg |
| | 250 mg |

Preparation

The active compound is mixed with the lactose and part of the wheat starch and with colloidal silica and the mixture is forced through a sieve. A further portion of the wheat starch is mixed to a paste with 5 times the amount of water on a water bath and the pulverulent mixture is kneaded with this paste until a slightly plastic mass has formed. The mass is forced through a sieve of about 3 mm mesh width and dried and the dry granules are again forced through a sieve. The remaining wheat starch, the talc and magnesium stearate are then mixed in. The resulting mixture is pressed to give 250 mg tablets with a breaking groove (or grooves).

In an analogous manner it is also possible to prepare tablets containing, in each case, 100 mg of one of the compounds listed below and these compounds can also be used in the form of salts which can be used pharmaceutically, such as acid addition salts, for example the hydrochlorides, or, in the case of carboxylic acids, salts with a base, for example sodium salts: 5-butyryl-6-methyl-benzimidazole-2-carboxylic acid, 5(6)-valeryl-benzimidazole-2-carboxylic acid, 5-acetyl-6-methyl-benzimidazole-2-carboxylic acid, 6-methyl-5-propionyl-benzimidazole-2-carboxylic acid, 6-methyl-5-valeryl-benzimidazole-2-carboxylic acid, 5(6)-butyryl-benzimidazole-2-carboxylic acid, 5-butyryl-6-methoxy-benzimidazole-2-carboxylic acid, 5-butyryl-6-chloro-benzimidazole-2-carboxylic acid, 5-cyclopropylcarbonyl-6-methyl-benzimidazole-2-carboxylic acid, 5-cyclohexylcarbonyl-6-methyl-benzimidazole-2-carboxylic acid, 5-(4-methoxybutyryl)-6-methyl-benzimidazole-2-carboxylic acid, 6-methyl-5-(4-methylthiobutyryl)-benzimidazole-2-carboxylic acid, 6-methyl-5-(4-methylsulphinylbutyryl)-benzimidazole-2-carboxylic acid, 6-methyl-5-(4-phenylthiobutyryl)-benzimidazole-2-carboxylic acid, 6-methyl-5-(4-phenylsulphinylbutyryl)-benzimidazole-2-carboxylic acid, methyl 5-butyryl-6-methyl-benzimidazole-2-carboxylate, 5-butyryl-6-methyl-benzimidazole-2-methanol, 5-butyryl-1,6-dimethyl-benzimidazole-2-methanol, 5(6)-valeryl-benzimidazole-2-methanol, 6-methyl-5-valeryl-benzimidazole-2-methanol, 5(6)-butyryl-benzimidazole-2-methanol, 5-acetyl-1-methyl-benzimidazole-2-methanol, 5-butyryl-1-methyl-benzimidazole-2-methanol, 5-butyryl-6-chloro-1-methyl-benzimidazole-2-methanol, 1,6-dimethyl-5-valeryl-benzimidazole-2-methanol, 1-ethyl-5-butyryl-6-methyl-benzimidazole-2-methanol, 5-acetyl-1-butyl-benzimidazole-2-methanol, 1-butyl-5-butyryl-6-methyl-benzimidazole-2-methanol, 1,6-dimethyl-5-oenanthyl-benzimidazole-2-methanol, 5-benzoyl-benzimidazole-2-methanol, 5-benzoyl-1-methyl-benzimidazole-2-methanol, 5-butyryl-6-methoxy-1-methyl-benzimidazole-2-methanol, 5-cyclopropylcarbonyl-1,6-dimethyl-benzimidazole-2-methanol, 2-ethoxymethyl-5-butyryl-6-methyl-benzimidazole, 2-ethoxymethyl-5-butyryl-1,6-dimethyl-benzimidazole, 2-acetoxymethyl-5-butyryl-1,6-dimethyl-benzimidazole, 5-butyryl-6-hydroxy-1-methyl-benzimidazole-2-methanol, 1,6-dimethyl-5-(4-methylthiobutyryl)-benzimidazole-2-methanol, 5-butyryl-1,6-dimethyl-2-(2-dimethylaminoethoxymethyl)-benzimidazole, 5-acetyl-1-methyl-benzimidazole-2-carboxylic acid, 5-butyryl-1-methyl-benzimidazole-2-carboxylic acid, 5-butyryl-6-chloro-1-methyl-benzimidazole-2-carboxylic acid, 1,6-dimethyl-5-valeryl-benzimidazole-2-carboxylic acid, 1-ethyl-5-butyryl-6-methyl-benzimidazole-2-carboxylic acid, 5-acetyl-1-butyl-benzimidazole-2-carboxylic acid, 1-butyl-5-butyryl-benzimidazole-2-carboxylic acid, 5(6)-benzoyl-benzimidazole-2-carboxylic acid, 5-cyclopropylcarbonyl-1,6-dimethyl-benzimidazole-2-carboxylic acid, 5-butyryl-6-hydroxy-1-methyl-benzimidazole-2-carboxylic acid, ethyl 5-butyryl-6-methyl-benzimidazole-2-carboxylate, ethyl 5-butyryl-1,6-dimethyl-benzimidazole-2-carboxylate and ethyl 5-butyryl-1-methyl-benzimidazole-2-carboxylate.

We claim:

1. A benz-acyl-benzimidazole-2-carboxylic acid derivative of the formula

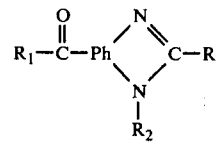 (I)

in which R is carboxyl, esterified carboxyl containing, as the etherified hydroxyl group, lower alkoxy, hydroxy-lower alkoxy, lower alkoxy-lower alkoxy or di-lower alkylamino-lower alkoxy or amidated carbonyl containing, as the amino group, amino, hydroxyamino, lower alkylamino, di-lower alkylamino or lower alkyleneamino, $R_1$ is lower alkyl, which is unsubstituted or substituted by lower alkoxy, lower alkylthio, lower alkylsulphinyl, lower alkylsulphonyl, phenylthio, phenylsulphinyl or phenylsulphonyl, lower alkenyl or cycloalkyl having from 3 to 8 carbon atoms, or phenyl or phenyl-lower alkyl which are unsubstituted or substituted in the phenyl radical by lower alkyl, lower alkoxy or halogen, $R_2$ is hydrogen or lower alkyl and Ph is 1,2-phenylene which contains the radical of the formula $R_1-C(=O)-$ and is otherwise unsubstituted or substituted by lower alkyl, lower alkoxy, hydroxy and/or halogen, or a pharmaceutically acceptable salt thereof.

2. A compound as claimed in claim 1, in which R is carboxyl, esterified carboxyl containing, as the etherified hydroxyl group, lower alkoxy or hydroxy-lower alkoxy having up to 4 carbon atoms, or amidated carboxyl containing, as the amino group, amino or hydroxyamino, or lower alkylamino or di-lower alkylamino in which lower alkyl contains up to 4 carbon atoms, $R_1$ is lower alkyl having up to and including 7 carbon atoms, lower alkoxy-lower alkyl, lower alkylthio-lower alkyl, lower alkylsulphinyl-lower alkyl or lower alkylsulphonyl-lower alkyl, in which the individual lower alkyl radicals contain up to and including 4 carbon atoms, phenylthio-lower alkyl, phenylsulphinyl-lower alkyl or phenylsulphonyl-lower alkyl, in which the lower alkyl radical contains up to and including 4 carbon atoms, lower alkenyl having up to and including 5 carbon atoms, cycloalkyl having up to and including 7 carbon atoms, phenyl or phenyl-lower alkyl having up to and including 4 carbon atoms in the lower alkyl radical and being unsubstituted or substituted by lower alkyl having up to and including 4 carbon atoms, lower alkoxy having up to and including 4 carbon atoms and/or halogen having an atomic number of up to and including 35, $R_2$ is hydrogen or lower alkyl having up to and including 4 carbon atoms and Ph is 1,2-phenylene which contains the radical of the formula $R_1-C(=O)-$ and is otherwise unsubstituted or substituted by lower alkyl having up to and including 4 carbon atoms, lower alkoxy having up to and including 4 carbon atoms, hydroxyl and/or halogen having an atomic number of up to and including 35, or a pharmaceutically acceptable salt thereof.

3. A compound as claimed in claim 1, having the formula

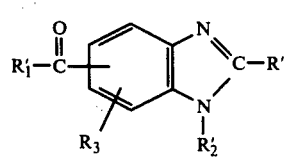 (Ia)

in which R' is carboxyl, esterified carboxyl containing, as the etherified hydroxyl group, lower alkoxy having up to 4 carbon atoms or, amidated carboxyl containing, as the amino group, amino or hydroxyamino, $R_1'$ is lower alkyl having up to 7 carbon atoms, lower alkoxy-lower alkyl, lower alkylthio-lower alkyl, lower alkyl-sulphinyl-lower alkyl, phenylthio-lower alkyl or phenylsulphinyl-lower alkyl, in which the lower alkyl radicals contain up to and including 4 carbon atoms, cycloalkyl having up to and including 6 ring carbon atoms or unsubstituted, phenyl, $R_2'$ is hydrogen or lower alkyl having up to and including 4 carbon atoms and $R_3$ is hydrogen, lower alkyl having up to and including 4 carbon atoms, lower alkoxy having up to and including 4 carbon atoms, hydroxyl or halogen having an atomic number of up to and including 35, or a pharmaceutically acceptable salt thereof.

4. A compound as claimed in claim 3, in which R' is carboxyl, or esterified carboxyl containing, as the etherified hydroxyl group, lower alkoxy having up to 4 carbon atoms, $R_1'$ is lower alkyl having up to and including 7 carbon atoms, cycloalkyl having up to and including 6 ring carbon atoms or phenyl, $R_2'$ is hydrogen or lower alkyl having up to and including 4 carbon atoms and $R_3$ is hydrogen, lower alkyl having up to and including 4 carbon atoms, lower alkoxy having up to and including 4 carbon atoms or halogen having an atomic number of up to and including 35, or a pharmaceutically acceptable salt thereof.

5. A compound as claimed in claim 1 being 5-butyryl-6-methyl-benzimidazole-2-carboxylic acid or a pharmaceutically acceptable salt thereof.

6. A compound as claimed in claim 1 being 5-butyryl-1,6-dimethyl-benzimidazole-2-carboxylic acid or a pharmaceutically acceptable salt thereof.

7. A compound as claimed in claim 1 being methyl-5-butyryl-6-methyl-benzimidazole-2-carboxylate or a pharmaceutically acceptable salt thereof.

8. A compound as claimed in claim 1 being ethyl 5-butyryl-1,6-dimethyl-benzimidazole-2-carboxylate or a pharmaceutically acceptable salt thereof.

9. A pharmaceutical preparation containing an antiallergically effective amount of a compound as claimed in claim 1 together with a conventional pharmaceutical carrier.

* * * * *